US011628077B2

(12) United States Patent
Ramzipoor et al.

(10) Patent No.: US 11,628,077 B2
(45) Date of Patent: Apr. 18, 2023

(54) POST DEPLOYMENT RADIAL FORCE RECOVERY OF BIODEGRADABLE SCAFFOLDS

(71) Applicant: Razmodics LLC, Novato, CA (US)

(72) Inventors: Kamal Ramzipoor, Fremont, CA (US); Chang Y. Lee, San Jose, CA (US)

(73) Assignee: Razmodics LLC, Novato, CA (US)

( * ) Notice: Subject to any disclaimer, the term of this patent is extended or adjusted under 35 U.S.C. 154(b) by 0 days.

(21) Appl. No.: 15/339,335

(22) Filed: Oct. 31, 2016

(65) Prior Publication Data
US 2018/0116837 A1 May 3, 2018

(51) Int. Cl.
*A61F 2/945* (2013.01)
*A61F 2/915* (2013.01)

(52) U.S. Cl.
CPC .............. *A61F 2/945* (2013.01); *A61F 2/915* (2013.01); *A61F 2210/0014* (2013.01); *A61F 2210/0071* (2013.01); *A61F 2240/001* (2013.01)

(58) Field of Classification Search
CPC ............ A61F 2/915; A61F 2/94; A61F 2/945
See application file for complete search history.

(56) References Cited

U.S. PATENT DOCUMENTS

| 5,843,117 | A | * | 12/1998 | Alt | A61F 2/86 |
| | | | | | 623/1.15 |
| 5,911,752 | A | * | 6/1999 | Dustrude | A61F 2/91 |
| | | | | | 604/96.01 |
| 6,206,911 | B1 | * | 3/2001 | Milo | A61F 2/91 |
| | | | | | 623/1.15 |
| 6,342,067 | B1 | * | 1/2002 | Mathis | A61F 2/91 |
| | | | | | 623/1.15 |
| 6,602,281 | B1 | * | 8/2003 | Klein | A61F 2/86 |
| | | | | | 623/1.15 |
| 8,206,635 | B2 | | 6/2012 | Ramzipoor et al. | |

(Continued)

FOREIGN PATENT DOCUMENTS

| WO | WO 2013/003644 | 1/2013 |
| WO | WO 2018/080638 | 5/2018 |

OTHER PUBLICATIONS

Lobo, Hubert et al., "Characterization and Modeling of Non-linear Behavior of Plastics," http://www.datapointlabs.com/testpaks/lobo-hurtado/lobo-hurtado_paper.html (visited Aug. 12, 2016).

*Primary Examiner* — Andrew D Graham
(74) *Attorney, Agent, or Firm* — Levine Bagade Han LLP

(57) ABSTRACT

Post deployment radial force recovery of biodegradable scaffolds are described where a high molecular weight polymer may be formed into a high molecular weight scaffold by solution casting into a tubular substrate such that the scaffold retains its mechanical properties through processing. The tubular substrate is laser cut and subsequently crimped onto a catheter for deployment into a body lumen. The polymeric scaffold may retain its mechanical properties and result in increased radial strength post-deployment in a saline environment, e.g., within a body lumen. This scaffold enhancement may be attributable at least in part to entanglement of high molecular weight polymer chains as one factor that effects radial force recovery and also to the design or geometry of the scaffold as another factor that effects radial force recovery after deployment.

19 Claims, 15 Drawing Sheets

(56) References Cited

U.S. PATENT DOCUMENTS

| | | | |
|---|---|---|---|
| 2001/0010014 A1* | 7/2001 | Trozera | A61F 2/91 623/1.16 |
| 2004/0088040 A1* | 5/2004 | Mangiardi | A61F 2/91 623/1.15 |
| 2006/0025852 A1* | 2/2006 | Armstrong | A61B 17/12022 623/1.17 |
| 2006/0247759 A1* | 11/2006 | Burpee | A61F 2/88 623/1.15 |
| 2007/0134296 A1* | 6/2007 | Burgermeister | A61F 2/91 424/426 |
| 2007/0200268 A1 | 8/2007 | Dave | |
| 2007/0207186 A1* | 9/2007 | Scanlon | A61F 2/07 424/424 |
| 2008/0046072 A1* | 2/2008 | Laborde | A61F 2/856 623/1.34 |
| 2008/0255655 A1* | 10/2008 | Kusleika | A61F 2/91 623/1.11 |
| 2009/0030501 A1* | 1/2009 | Morris | A61F 2/915 623/1.15 |
| 2009/0234432 A1* | 9/2009 | Pacetti | A61F 2/91 623/1.16 |
| 2010/0004734 A1* | 1/2010 | Ramzipoor | A61F 2/91 427/2.24 |
| 2010/0042202 A1* | 2/2010 | Ramzipoor | A61F 2/91 623/1.15 |
| 2010/0094405 A1* | 4/2010 | Cottone | A61F 2/91 623/1.16 |
| 2010/0274349 A1* | 10/2010 | Lord | A61F 2/91 623/1.16 |
| 2011/0066225 A1* | 3/2011 | Trollsas | A61F 2/91 623/1.16 |
| 2011/0190871 A1* | 8/2011 | Trollsas | A61F 2/91 623/1.15 |
| 2011/0288622 A1* | 11/2011 | Chan | A61F 2/915 623/1.11 |
| 2012/0073733 A1* | 3/2012 | Ngo | A61F 2/915 156/196 |
| 2012/0271396 A1* | 10/2012 | Zheng | A61L 31/14 623/1.2 |
| 2013/0025110 A1* | 1/2013 | Stankus | A61F 2/958 29/505 |
| 2013/0053758 A1* | 2/2013 | Kibbe | A61F 2/945 604/21 |
| 2014/0025161 A1* | 1/2014 | Stankus | A61L 31/148 623/1.19 |
| 2014/0039600 A1 | 2/2014 | Ramzipoor et al. | |
| 2015/0051686 A1* | 2/2015 | Ramzipoor | A61F 2/954 623/1.11 |
| 2015/0054202 A1 | 2/2015 | Lambert et al. | |
| 2015/0073536 A1 | 3/2015 | Rapoza et al. | |
| 2015/0252144 A1* | 9/2015 | Jiang | A61L 31/06 623/1.15 |
| 2015/0305827 A1 | 10/2015 | Wang et al. | |
| 2015/0342764 A1* | 12/2015 | Ramzipoor | A61L 31/06 623/1.16 |
| 2016/0213499 A1* | 7/2016 | Zheng | A61F 2/915 |
| 2016/0374838 A1* | 12/2016 | Pacetti | A61L 31/06 623/1.38 |
| 2016/0375179 A1* | 12/2016 | Gamez | A61F 2/915 427/2.28 |
| 2017/0049593 A1* | 2/2017 | Hossainy | B29C 55/26 |
| 2017/0095359 A1* | 4/2017 | Gale | A61F 2/915 |
| 2017/0231790 A1* | 8/2017 | Abunassar | A61F 2/915 623/1.11 |
| 2017/0290688 A1* | 10/2017 | Stankus | A61F 2/915 |
| 2018/0008438 A1* | 1/2018 | Lumauig | A61L 31/06 |
| 2018/0036154 A1* | 2/2018 | Hossainy | A61F 2/915 |
| 2018/0056569 A1* | 3/2018 | Cottone | A61L 31/148 |
| 2018/0133040 A1* | 5/2018 | Stankus | A61L 31/148 |

* cited by examiner

Entanglement of polymer chains

High pull force (strength)

CONVENTIONAL PLLA
Resin MW 250K TO 300K Da
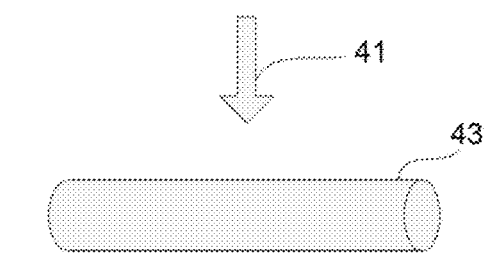
PRESENT PLLA
Resin MW Ultra High
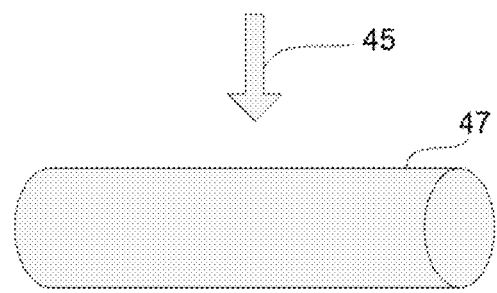
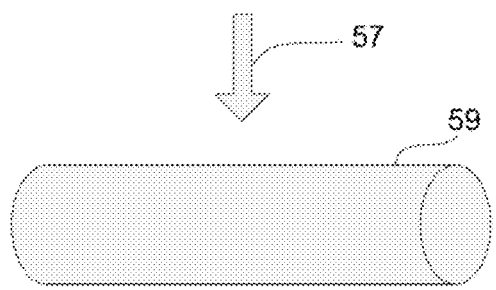
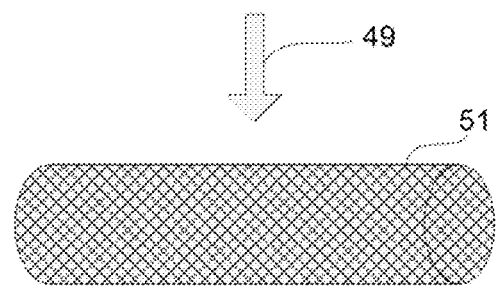
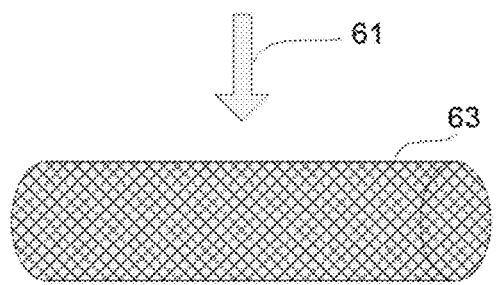
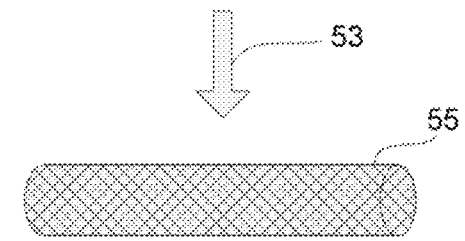
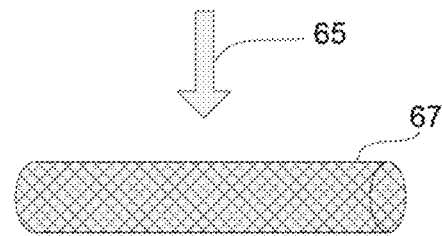
FIG. 8A
FIG. 8B

| Case # | Description | 3.8mm Rev9 Strain(%) |
|---|---|---|
| 1 | Crimping to onset of contact | 156.8 |
| 2 | Crimping to catheter diameter ID | 156.1 @ OD=1.16mm |
| 3 | No crimping, axial 6% extension | 0.9064 |
| 4 | No crimping, axial 6% contraction | 1.0437 |
| 5 | Crimping to implantation diameter and axial 6% extension | 15.615 @ OD=3.5mm |
| 6 | Crimping to implantation diameter and axial 6% contraction | 12.81 @ OD=3.5mm |
| 7 | Crimping to fixed lumen diameter and axial 6% extension | 4.396 @ ID=3.5mm |
| 8 | Crimping to fixed lumen diameter and axial 6% contraction | 2.79 @ ID=3.5mm |

FIG. 10C

| Case # | Description | 3.94mm Rev13 Strain (%) |
|---|---|---|
| 1 | Crimping to diameter just prior to onset of self-contact | 128.00 |
| 2 | Crimping to an outside diameter of 1.2mm | 127.00 |
| 3 | No crimping and simultaneous axial contraction 6% | 0.9500 |
| 4 | No crimping and simultaneous axial extension 6% | 1.0609 |
| 5 | 15% crimping and simultaneous axial contraction 6% | 22.9622 |
| 6 | 15% crimping and simultaneous axial extension 6% | 24.5954 |
| 7 | 11% crimping and simultaneous axial contraction 6% | 16.5067 |
| 8 | 11% crimping and simultaneous axial extension 6% | 18.7027 |

FIG. 10D

| Case # | Description | Rev23 Strain(%) |
|---|---|---|
| 1 | Crimping to diameter just prior to onset of self-contact | 107.6 |
| 2 | Crimping to an outside diameter of 1.2mm | 105.9 |
| 3 | Crimping to an outside diameter of 1.0mm | 119.0 |
| 4 | Mild crimping and simultaneous axial contraction 6% | 7.5269 |
| 5 | Mild crimping and simultaneous axial extension 6% | 7.4153* |
| 6 | Aggressive crimping and simultaneous axial contraction 6% | 31.1359 |
| 7 | Aggressive crimping and simultaneous axial extension 6% | 31.2157 |

FIG. 10E

| No | OD (mm) | Wall thickness (mm) | Tensile stress at Yield (MPa) | Tensile strain at Yield (%) | Tensile load at break (MPa) | Tensile stress at break (MPa) | Tensile strain at break (%) | Modulus E (MPa) |
|---|---|---|---|---|---|---|---|---|
| 1 | 5.10 | 0.178 | 79.31 | 3.66 | 200.94 | 73.00 | 112.49 | 2696.00 |
| 2 | 5.09 | 0.175 | 81.70 | 3.61 | 208.84 | 77.29 | 105.71 | 2786.56 |
| 3 | 5.09 | 0.175 | 81.06 | 3.69 | 208.58 | 77.19 | 122.53 | 2692.60 |
| 4 | 5.10 | 0.177 | 80.62 | 3.73 | 202.93 | 74.09 | 97.21 | 2660.43 |
| Avg | 5.10 | 0.176 | 80.67 | 3.67 | 205.32 | 75.39 | 109.48 | 2708.90 |
| Dev | 0.01 | 0.002 | 1.01 | 0.05 | 4.00 | 2.18 | 10.71 | 54.20 |

FIG. 12

POST DEPLOYMENT RADIAL FORCE RECOVERY OF BIODEGRADABLE SCAFFOLDS

FIELD OF THE INVENTION

The present invention relates generally to manufacturing processes for forming or creating devices which are implantable within a patient, such as medical devices. More particularly, the present invention relates to methods and processes for forming or creating tubular substrates which may be further processed to create medical devices having various geometries suitable for implantation within a patient.

BACKGROUND OF THE INVENTION

Many conventional methods to form a scaffold have to use melt processes such as extrusion and injection molding to fabricate a polymeric tube for use in fabricating a stent scaffold having required mechanical properties. However, the polymeric tube that is produced by such processes do not exhibit the required mechanical properties, so the polymeric tube must be processed further by methods such as radial expansion to gain favorable mechanical properties. Radial expansion gains favorable mechanical properties such as radial strength which is a result of oriented crystallites that produce a higher crystallinity. FIGS. 1A and 1B illustrate a conventional expansion approach for imparting, strain induced crystalline orientation in a conventional scaffold 10 from an initial first diameter, e.g., 2 mm, to an expanded diameter, e.g., 4 mm, where the expanded scaffold 10' has an orientation imparted into its crystalline structure, as shown in the detail view 12 illustrating an example of oriented PLLA polymer chains after expansion. Crystallinity is imposed in the scaffold 10' for use in imparting radial strength in the scaffold to resist compressive load and withstand fatigue upon deployment in a patient.

Upon deployment of prior art scaffolds formed of melt processes and radial expansion, the radial strength may slightly increase due to a slight increase of crystallinity of the scaffold at, e.g., 37° C., in the saline conditions of a patient. The crystallinity increases upon deployment and hydrolysis in a patient because the polymer chains are realigning in the saline condition of the lumen. A scaffold made of higher crystallinity, such as in the prior art where an extruded tube is radially expanded to impart crystallinity, the scaffold exhibits a brittle behavior upon deployment in a lumen, limiting the scaffold's resistance to fracture and its ability to over-expand.

FIG. 2 illustrates a prior art polymeric tube extrusion that is radially expanded. In prior art scaffolds, strength imparted is directly proportional to the amount of radial expansion of the tube and orientation of the polymeric chains of the tube. For example, as illustrated in FIG. 2, in the production of a polymeric tube extrusion 14 the extruded diameter is, e.g., 2 mm. The polymeric tube may be radially expanded 14' to a diameter of, e.g., 4 mm. The maximum orientation induced on the tube 14' that has been radially expanded is two times.

FIG. 3 illustrates how the struts of a conventional scaffold 20 may not thin, elongate, or deform so long as the scaffold 20 is not expanded beyond its originally intended diameter of expansion. As long as the scaffold 20 of the prior art is not expanded beyond its originally intended diameter of expansion, the struts 24 are not thinner, elongated, or deformed compared to the intended dimension of expansion, as shown in the detail view 22. However, as illustrated in FIG. 4, when the scaffold 20' of the prior art is expanded beyond its originally intended diameter of expansion, the struts 24' become relatively thinner, elongated, or deformed compared to intended dimension, which causes lower radial force in the over expanded scaffold 20'. FIG. 4 illustrates how the struts of a conventional scaffold may thin, elongate, or deform when the scaffold is expanded beyond its originally intended diameter of expansion. The prior art scaffold 20' also experiences increased diametric recoil due to contraction of elongated struts 24' when the expansion force is removed. In addition, the prior art scaffold 20' has increased fatigue upon deployment and a decrease in long term structural integrity. Therefore, the prior art scaffold 20' does not avoid fatigue post deployment because a reduction in the strut thickness results in a compromise in radial strength upon deployment and radial expansion.

Although there is a slight increase in radial strength in the prior art scaffold, the increase in radial strength is due to the increase in crystallinity of the low molecular weight scaffold that is immediately hydrolyzed in the lumen post deployment. Nonetheless, this nominal increase in radial strength is still insufficient for providing long term structural integrity of the stent after implantation within the patient.

Accordingly, there is a need for a scaffold which provides for relatively high radial strength after expansion and implantation within the patient, having sufficient resistance to fracture and the ability to over-expand.

SUMMARY OF THE INVENTION

A high molecular weight polymer may be formed into a high molecular weight scaffold by solution casting, into a tubular substrate such that the scaffold retains its mechanical properties through processing. The tubular substrate may be laser cut and subsequently crimped onto a catheter, such as a balloon catheter, for deployment into a body lumen. Forming such a polymeric scaffold that retains its mechanical properties may be attributable at least in part to entanglement of high molecular weight polymer chains as one factor that effects radial force recovery and also to the design or geometry of the scaffold as another factor that effects radial force recovery after deployment.

Such a high molecular weight polymer scaffold that has been formed from solution casting retains at least some of the mechanical properties of the polymeric resin and the design or geometry of the stent scaffold has an enhancing effect on the acute and the chronic radial force and improves the exhibited chronic radial force of the scaffold over time. The stent scaffold described herein increases in its chronic radial force by up to 30% higher than its acute radial force in some embodiments. Such a scaffold may be structurally robust with no compromise in scaffold strength for at least a predetermined period of time after deployment, e.g., up to six months after deployment, as well as maintain structural integrity upon over-expansion.

The design or geometry of the scaffold is configured to contain the stress and strain in strategic locations of the scaffold and the properties of the polymer can be controlled in order to effect radial strength of the scaffold at deployment into a saline environment and a temperature of, e.g., at least 37° C. Such properties of the polymer (e.g., the elongation break, modulus, tensile strain at yield) can be controlled during the manufacture of the scaffold in a solution casted scaffold. In one embodiment, the tensile strain at yield of the polymer used to manufacture the scaffold is kept within a range of, e.g., 3% to 4%, to allow for the propensity of the tube to regain strength once the tube is exposed to a temperature of, e.g., at least 37° C., in a saline condition. In this embodiment, the scaffold has the ability to recover pre-crimp and pre-expansion radial strength when the scaffold is deployed into a saline environment at a temperature of, e.g., at least 37° C. in one embodiment of a PLEA 8.28, 30% to 70% of the acute radial strength of the scaffold is recovered when deployed in saline condition at a temperature of at least 37° C. and not higher than $T_g$ of the polymer.

The radial force increase after deployment of the scaffold is not due to creep or shape memory of a polymer. On the contrary, the radial force recovery upon deployment over a period of time and temperature is due to strain recovery. Once a scaffold is deployed, compression load is always applied to a scaffold by the vessel pulsating. There is a damage of the polymer chains which are stretched, thereby opening the network of polymers. The recovery depends on how strong the interactions of the polymer chains are with one another, which is a time-temperature phenomenon.

When deformation is caused by crimping and deployment or expansion, there is a predictable elastic component of the scaffold that is able to be recovered due to the high molecular weight of the scaffold as well as in combination with the geometry of the scaffold. Both the elastic component of the scaffold as well as the geometry of the scaffold contribute to the radial force recovery post deployment. Thus, even if the elastic component of the scaffold is not able to be measured, the geometry of the scaffold also reacts to the load.

The radial force of the scaffold increases as a function of time in the saline and elevated temperature of the patient. In a sense, the scaffold repairs its radial strength almost immediately after deployment. Internal polymer chains of the scaffold realize or repair the first crimp and expansion damage. In fact, there is no compromise of scaffold's integrity for the duration of the year in the lumen because the radial force does not decrease below the scaffold's radial strength at deployment for at least about 6 months.

The regain of radial force is due to a completely different phenomenon from prior art scaffolds that may increase slightly in crystallinity at deployment. Conventional scaffolds that have been radially expanded by melt processes during its manufacturing may increase in crystallinity due to the polymer's absorption of water and their radial strength is strictly due to the amount of crystallinity of the polymer that has been induced by processes such as radial expansion. However, this increase in crystallinity of the conventional scaffold causes brittleness in the scaffold and results in fractures of the scaffold after implantation. These devices have a low molecular weight to moderate molecular weight, e.g. 200,000 Daltons to 300,000 Daltons, and are usually sterilized by e-beam sterilization which reduce the molecular weight of the polymer even further. Deformation of the low molecular weight polymer of the conventional scaffold is a very viscous or plastic deformation, having little or no elastic deformation. Moreover, deformation of a conventional scaffold upon crimping is mainly due to plastic or viscous deformation.

The increase of radial force in the scaffold of the present invention cannot be due to shape memory effect because the scaffold is deployed at a diameter which is the same diameter of the as formed substrate. The scaffold is not deployed at a diameter that is less than the as formed diameter to cause the shape memory effect. In embodiments of a scaffold comprising 100% PLLA, it should also be noted that the $T_g$ of PLLA is almost double the temperature of the body, or 37° C. Therefore, the 100% PLLA scaffold would require a temperature of double the temperature of the body in order to effect shape memory. Thus, the present invention's scaffold that increases in radial force upon deployment cannot be due to shape memory at such a low temperature of the body, but rather is attributed to strain recovery of the polymer chains. For these reasons, the radial strength increase in the present scaffold is a function of strain recovery as opposed to shape memory effect of the polymer as well as the design or geometry of the scaffold.

In one embodiment, a method of forming a stent scaffold may generally comprise dissolving a raw polymeric resin in a solvent to form at least a first polymeric solution, wherein the resin has a relatively high molecular weight; forming at least a first layer of a biocompatible polymer tube having a first diameter with the first polymeric solution; curing the tube; processing the tube to form an expandable scaffold having the first diameter, wherein the scaffold has a first radial strength; reducing the first diameter of the scaffold to a second smaller diameter, wherein the scaffold retains at least 90% of the molecular weight of the resin and at least a portion a crystallinity of the resin such that the scaffold exhibits ductility upon application of a load; and deploying the scaffold in a saline environment at a temperature of at least 37° C. and below $T_g$ of the polymeric resin, wherein the scaffold regains 30% to 60% of the radial strength of the scaffold prior to reducing: the first diameter of the scaffold to a second smaller diameter.

In another embodiment, an implantable medical device may generally comprise a polymeric scaffold having a first radial strength prior to being crimped at a first temperature and a second radial strength when expanded and exposed to an elevated second temperature of at least 37° C. and less than T of the polymer and within a saline environment, wherein the scaffold regains at least 30% of the first radial strength of the scaffold.

In yet another embodiment, a scaffold may have a tensile strain at yield within a range of 3% to 4% in one or more of the following conditions: crimping to onset of contact, crimping to a catheter diameter ID, no crimping, axial 6% extension, no crimping, axial 6% contraction, crimping to implantation diameter and axial 6% extension, crimping to implantation diameter and axial 6% contraction, crimping to fixed lumen diameter and axial. 6% extension, and crimping to fixed lumen diameter and axial 6% contraction.

In yet another embodiment, a scaffold may have a tensile strain at yield within a range of 3% to 4% in one or more of the following conditions: crimping to a diameter just prior to onset of self-contact, crimping to an outside diameter of 1.1 mm, crimping to an outside diameter of 1.2 mm, no crimping and simultaneous axial contraction 6%, no crimping and simultaneous axial extension 6%, 15% crimping, and simultaneous axial contraction 6%, 15% crimping and simultaneous axial extension 6%, 11% crimping and simultaneous axial contraction 6%, and 11% crimping and simultaneous axial extension 6%.

In yet another embodiment, a scaffold may have a tensile strain at yield within a range of 3% to 4% in one or more of the following conditions: crimping to a diameter just prior to onset of self-contact, crimping to an outside diameter of 1.2 mm, crimping to an outside diameter of 1.0 mm, mild crimping and simultaneous axial contraction 6%, mild crimping and simultaneous axial extension 6%, aggressive crimping and simultaneous axial contraction 6%, aggressive crimping and simultaneous axial extension 6%.

BRIEF DESCRIPTION OF THE DRAWINGS

FIGS. 8A and 8B illustrate a comparison between a conventional polymeric scaffold and a scaffold fabricated according to the present invention.

FIGS. 10C to 10E illustrate tables of different scaffold designs and their respective resulting strain values from non-linear finite element analyses of the respective scaffolds.

FIG. 12 shows a table with examples of stent scaffolds which have been fabricated to the dimensions indicated and by methods described herein to illustrate the various material property parameters achieved.

DETAILED DESCRIPTION OF THE INVENTION

In forming a scaffold which is able to retain its mechanical properties through processing, a high molecular weight polymer may be formed into a high molecular weight scaffold by solution casting (e.g., dip-coating) into a tubular substrate. The tubular substrate may be laser cut and subsequently crimped onto a catheter, such as a balloon catheter, for deployment into a body lumen. Hence, forming such a polymeric scaffold which retains its mechanical properties may be attributable at least in part to entanglement of high molecular weight polymer chains as one factor that effects radial force recovery, as well as to the design or geometry of the scaffold as another factor that effects radial force recovery after deployment. Conventional polymeric scaffolds typically utilize a melted polymer resin through extrusion processes and stretches or orients a highly crystalline tubular substrate that is later laser cut and crimped.

Effects of Entanglement of High Molecular Weight Polymer Chains On Radial Force Recovery On the other hand, a high molecular weight polymer that has been dip-coated does not require any processing, by conventional melt processes such as extrusion and injection molding in order to impart strength. Rather, the polymer is dip-coated and the scaffold retains at least some of the mechanical properties of the polymeric resin, as described in further detail in U.S. Pat. No. 8,206,635 or U.S. Pub. 2014/0039600, each of which are incorporated herein by reference in its entirety and for any reason. Thus, the thermal history of the dip-coated tube of the invention is much different from a tube that has been formed by conventional melt processes.

Figures 1A, 1B:
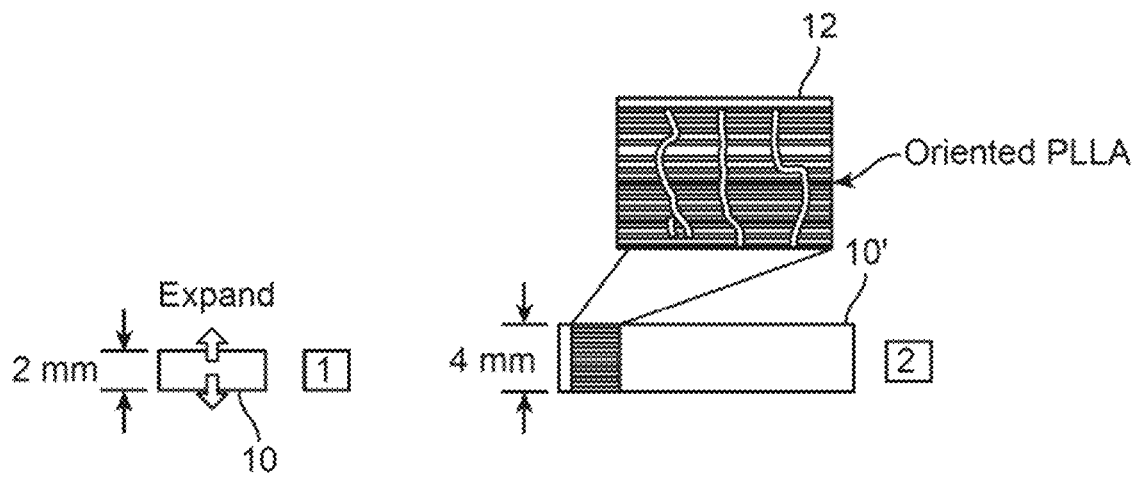
FIGS. 1A and 1B illustrate a conventional expansion approach for imparting, strain induced crystalline orientation in a conventional scaffold from an initial first diameter to an expanded diameter, where the expanded scaffold has an orientation imparted into its crystalline structure, as shown in the detail view illustrating an example of oriented PLLA after expansion.
Figure 2:
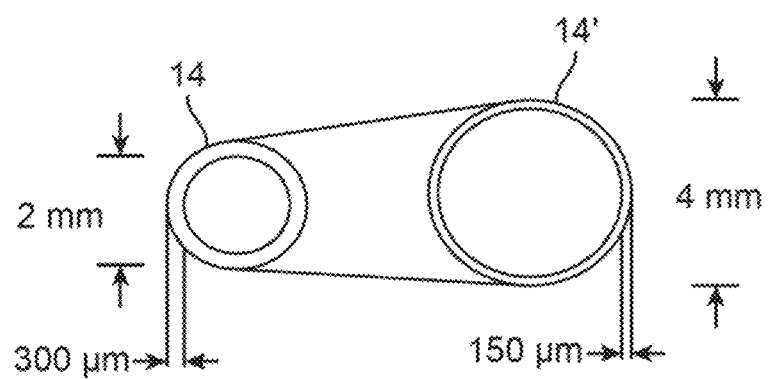
FIG. 2 illustrates a prior art polymeric tube extrusion that is radially expanded.
Figure 3:
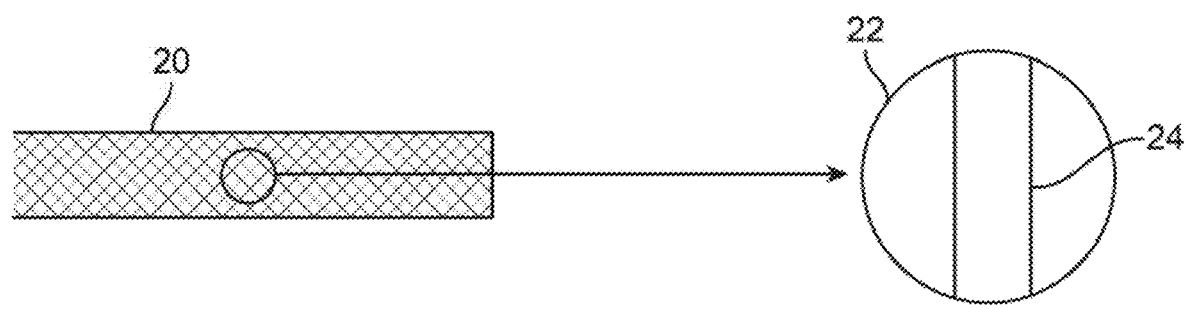
FIG. 3 illustrates bow the struts of a conventional scaffold may not thin, elongate, or deform so long as the scaffold is not expanded beyond its originally intended diameter of expansion.
Figure 4:
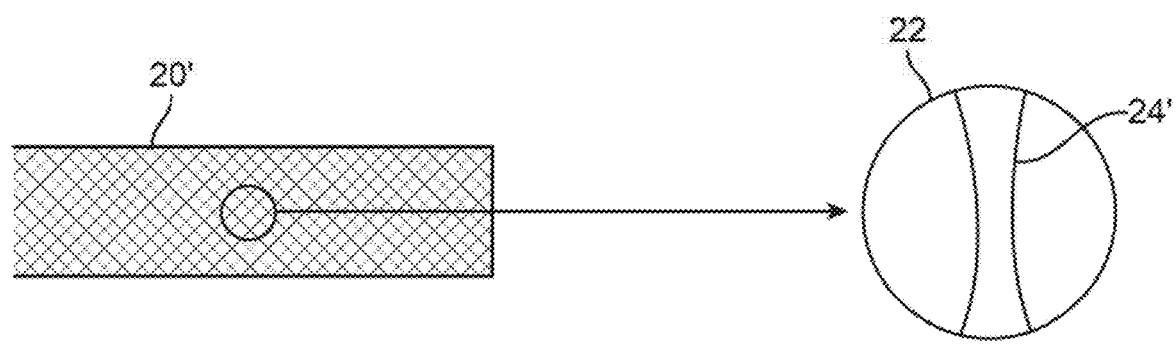
FIG. 4 illustrates how the struts of a conventional scaffold may thin, elongate, or deform when the scaffold is expanded beyond its originally intended diameter of expansion.
Figure 5A:
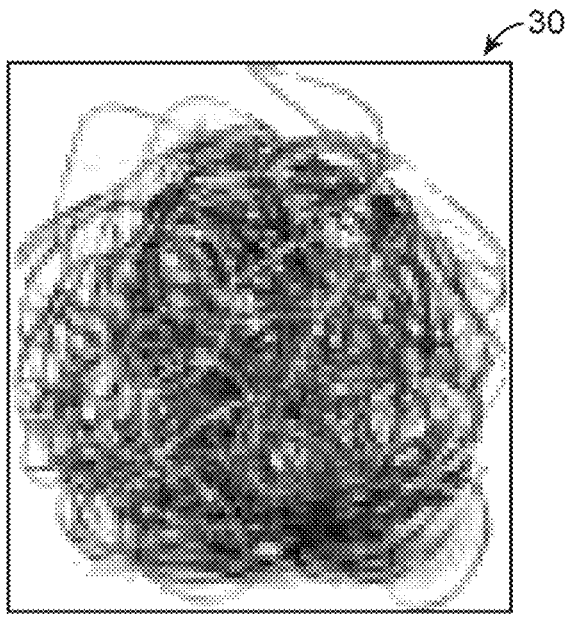
FIGS. 5A and 5B illustrate examples of how the high molecular weight polymer chains retained by the dip-coating process enable significant chain interactions and entanglements.
Figure 5B:
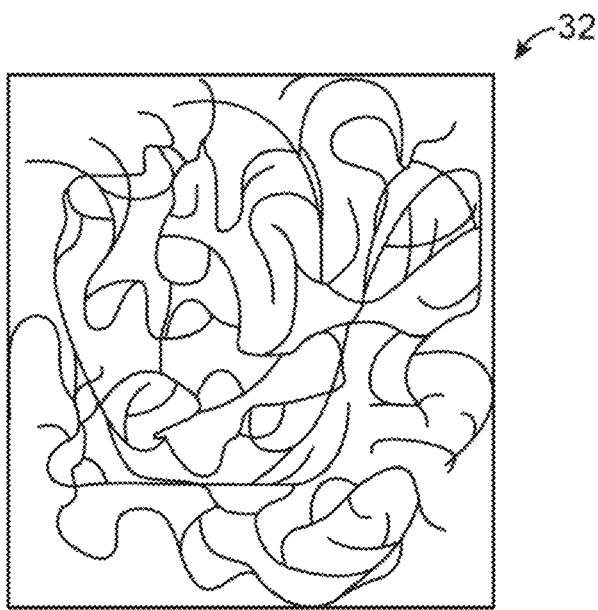
Figure 6:
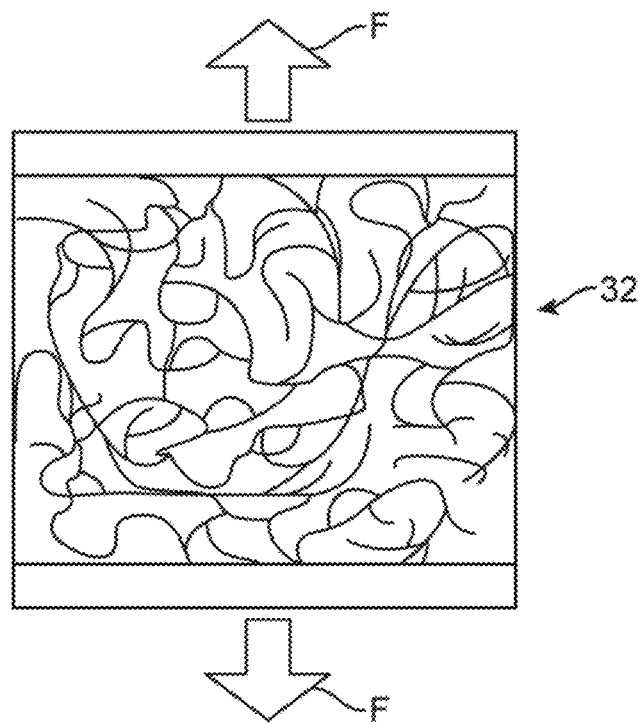
FIG. 6 illustrates an example of the long polymeric chains entangling upon the application of a pull force.

As mentioned above, with respect to the entanglement of high molecular weight polymer chains one of the mechanical properties that is retained by a dip-coated tube is molecular weight. Thus, unique physical properties and substantial strength and ductility are imparted into the scaffold, which is the direct result of long polymer chains of the high molecular weight polymer. FIGS. 5A and 5B illustrate examples of how the high molecular weight polymer chains 30 retained by the dip-coating process enable significant chain interactions and entanglements 32. The long polymer chains 30 of the high molecular weight polymer may have significant chain interactions and entanglements 32 and may become entwined or enmeshed 32 with one another. FIG. 6 illustrates an example of the long polymeric chains entangling upon the application of a pull force F. This entanglement 32 results in a substrate material having a high radial strength as shown by the application of a relatively high pull force F.

Figure 7A:
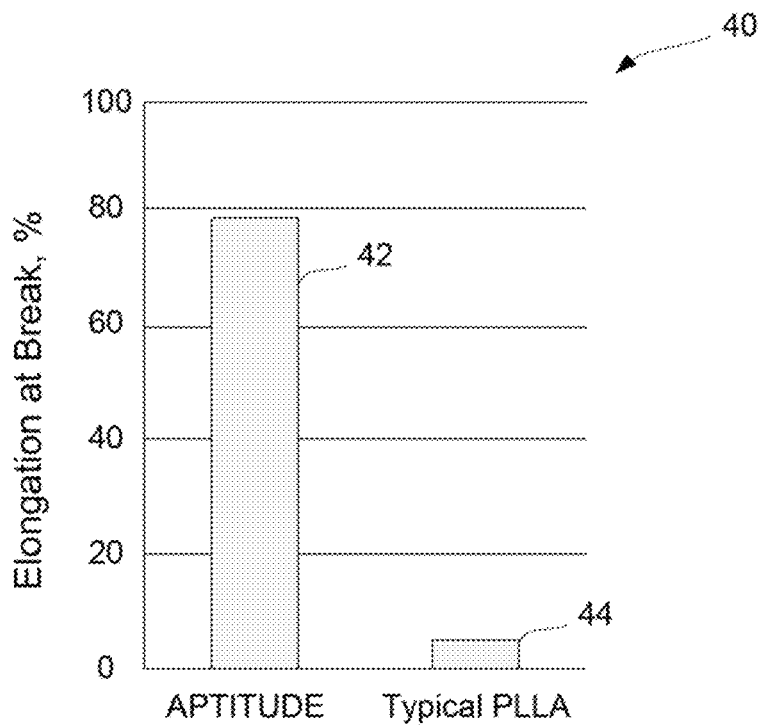
FIG. 7A illustrates a comparison between the elongation at break percentage between a conventional lower molecular weight PLLA polymer and the high molecular weight PLLA polymer.

Such high radial strength and fracture toughness is not limited by crystallinity as it is in conventional polymeric scaffolds. The polymer resin of 8.20-8.4 PLLA having a high molecular weight, for example, exhibits a material property of elongation at break percentage 42 that is at least ten times above that of the elongation at break percentage 44 of a conventional lower molecular weight PLLA polymer, as shown in the graph 40 of FIG. 7A. In some cases, the elongation at break percentage 42 for the high molecular weight resin 8.2-8.4 PLLA can be as much as twenty times above typical lower molecular weight PLLA polymer capabilities.

Figure 7B:
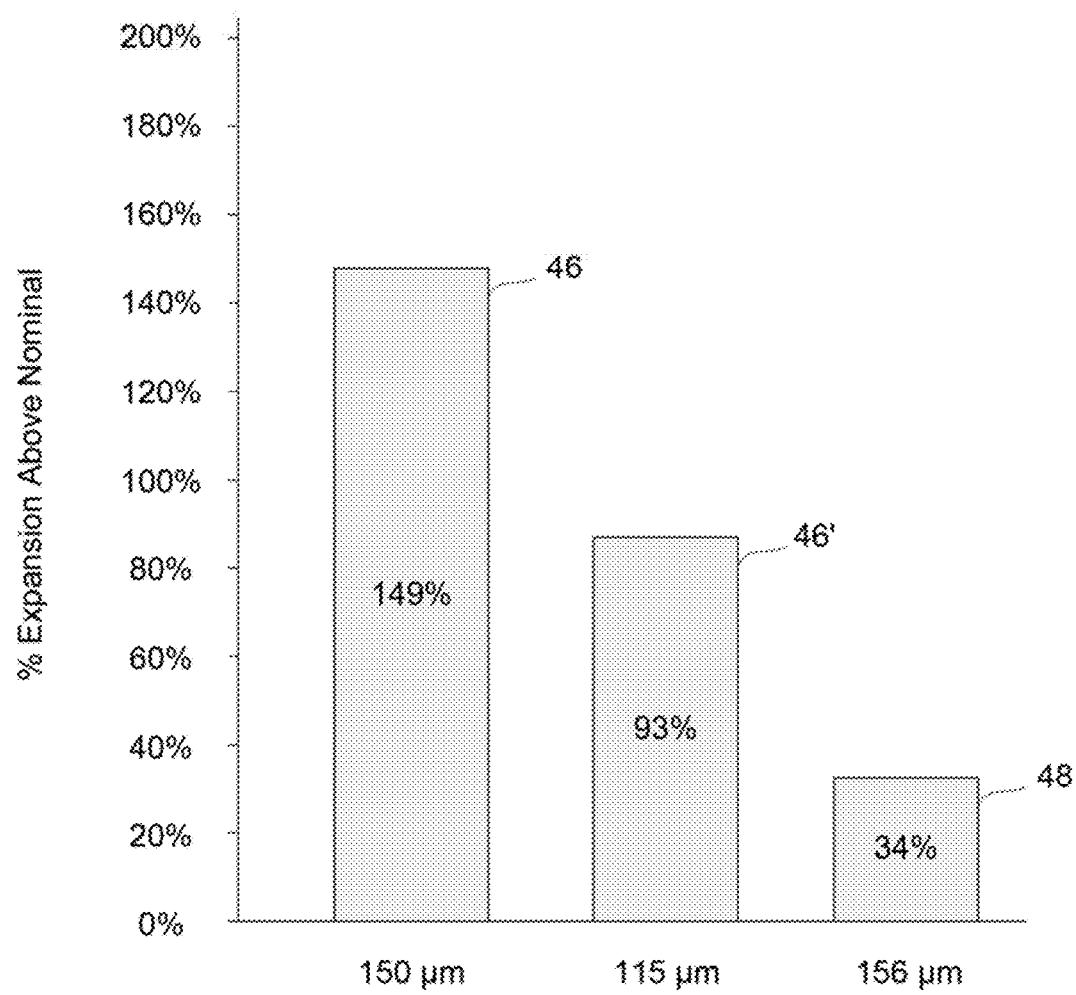
FIG. 7B illustrates a chart of a percent expansion above a nominal diameter between ultra-high molecular weight PLLA scaffolds of the present invention compared to a conventional scaffold.

FIG. 7B illustrates another comparison in a chart showing percent expansion above a nominal diameter between ultra-high molecular weight PLLA scaffolds of the present invention compared to a conventional scaffold as a comparison of fracture resistance on over-expansion. A first scaffold was produced having a 150 µm strut thickness according to the present invention and a second scaffold having a 115 µm strut thickness was produced, also according to the present invention. A third scaffold having a 156 µm strut thickness of a conventional scaffold (Abbott Vascular Bioresorbable Vascular Scaffold (BVS) System, Abbott Laboratories, Ill.) was used and all three scaffolds were over-expanded until failure.

The first scaffold yielded an over-expansion of 4.0 mm above a nominal diameter to first fracture resulting in a 149% expansion increase above nominal 46 while the second scaffold yielded an over-expansion of 2.5 mm above a nominal diameter to first fracture resulting in a 93% expansion increase above nominal 46'. In comparison, the third conventional scaffold resulted in an over-expansion of just 1.4 mm resulting in a 34% expansion 48. Even with a thickness which was larger than either the first and second scaffold, the third scaffold yielded the lowest percent expansion. This is evident of the uniform strength in all directions of deformation of the scaffold according to the present invention while the conventional scaffold shows a preferential strength in just the radial direction of deformation and further results in a significantly less-robust scaffold.

Yet another comparison between the processing of a conventional polymeric scaffold and a polymeric scaffold as disclosed herein is shown in the comparison of FIGS. 8A and 8B. As illustrated in FIG. 8A, a conventional PLLA solution (e.g., a resin having a molecular weight of 250 k to 300 k Da) is typically extruded 41 to result in a tubular substrate 43. This extruded substrate 43 is then processed 45 via stretching and orientation manipulation to result in a highly crystalline tubular substrate 47 (as discussed in further detail herein) which is then processed 49 to result in a stent scaffold 51. This scaffold 51 is then further processed 53 to result in the final scaffold 56 having a reduced or crimped diameter for deployment.

In comparison, FIG. 8B illustrates an example of how a resin having an ultra-high molecular weight may be solution cast 57, e.g., upon a mandrel, to result in the tubular substrate 59 which has a highly amorphous structure. This substrate 59 may then be processed 61 to result in a PLEA stem scaffold 63 which may be then further processed 65 to result in the final scaffold 67 having the reduced or crimped diameter for deployment.

The PLLA scaffold 67 fabricated according to the disclosure herein results in a scaffold which displays an elongation at break properties which is ten times (or greater) above the break properties of a conventionally fabricated scaffold 55.

Effects of Design or Geometry of Scaffold on Radial Force Recovery after Deployment The geometry of the stent scaffold has an enhancing effect on the acute and the chronic radial force and improves the exhibited chronic radial force of the scaffold over time. There is a distinction between an acute radial force and a chronic radial force. The acute radial force is the radial force exhibited by the scaffold immediately upon deployment within a body lumen while the chronic radial force is the radial force exhibited by the scaffold after deployment and a given period of time. While a conventional scaffold may exhibit a relatively high acute radial force immediately after deployment, such conventional scaffolds typically decrease in their chronic radial force over time. However, the stent scaffold described herein actually increases in its chronic radial force by up to 30% higher than its acute radial force in some embodiments. Such a scaffold may be structurally robust with no compromise in scaffold strength for at least a predetermined period of time after deployment, e.g., up to six months after deployment.

One example of the chronic radial force increase has been shown in tests using a 100 micron stent scaffold comparing a conventional metallic stem versus a polymeric stent as described, herein. If at deployment, the radial force of the metallic stent is comparatively the same as the polymeric scaffold, the resulting chronic radial force is higher in the polymeric stem over the metallic stem after a six-month period post deployment. The high molecular weight entanglement, described herein, triggers the high radial strength when realignment of the polymer chains results in increases in radial force. An increase in radial force gives a chronic radial force that is 30% higher than a comparative metallic stem.

The design of a stent scaffold of the invention may exhibit a certain tensile strain at yield when subjected to compressive and axial forces such as during crimping and expansion. The tensile strain at yield is an indication of how much strain is capable of being stored in the polymer when the scaffold is subjected to these forces. In other words, the polymer of the scaffold has the capacity to store tensile strain at yield and it is this strain of a scaffold that can be recovered upon exposure to conditions such as a saline environment, body temperature, and time. With respect to the exposure to increased temperature, strain recovery occurs during exposure to body temperature and there is no need for a temperature increase to $T_g$ to affect a shape memory effect.

Figure 9A:
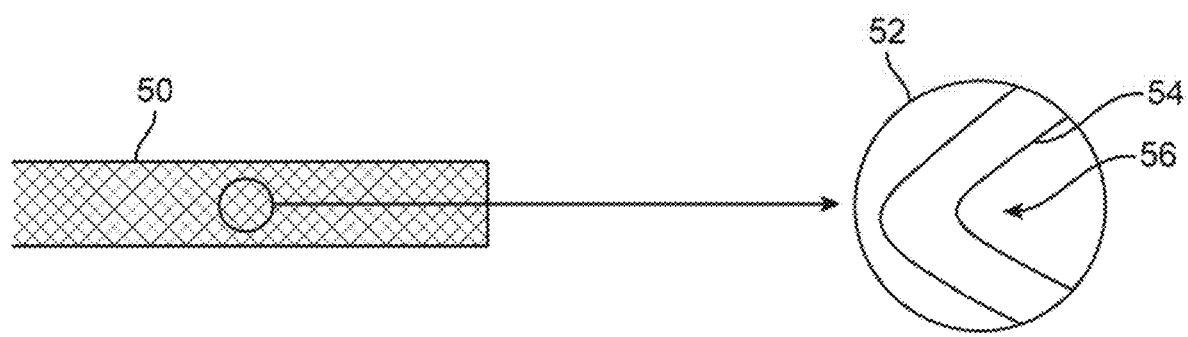
FIGS. 9A and 9B illustrate side and detail side views of a stent scaffold showing how individual strut members may be arranged and configured to accommodate an initial angle in a crimped configuration and an over expansion without strut thinning or elongation.
Figure 9B:
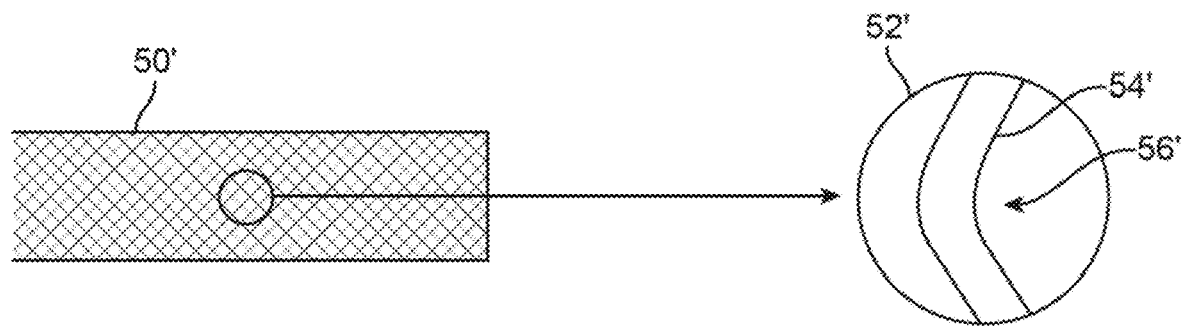

Because the radial force increase of the scaffold upon deployment or expansion is influenced by the scaffold's geometric design, so long as the strain that is induced by over-expanding the scaffold remains under the ultimate strain of the material, no fractures or cracks will occur in the scaffold. Thus, the strain is stored in the scaffold until deployment into, e.g., a saline environment at body temperature, at which point the radial strength of the scaffold may be recovered. As illustrated in the side view of FIG. 9A, a stent scaffold 50 is show in an unexpanded or non-deployed configuration and the detail view 52 illustrates an example of an individual strut member 54 which forms an initial angle 56 in its crimped configuration. The member 54 may be seen with the absence of cracks of fractures. When the stent scaffold 50 is expanded to its originally intended diameter, the member 54 may remain free of any cracks or fractures. However, the strut members may be arranged to accommodate over expansion without strut thinning or elongation, as illustrated in the side view of FIG. 9B, where the stem scaffold 50' is shown in an expanded diameter which is expanded beyond its originally intended diameter. This may be seen in the detail view 52' where the member 54' forms an angle 56' which increases relative to the angle formed in the crimped configuration as the scaffold 50' increases in diameter but even as the scaffold 50' is increased beyond its intended expanded diameter, the member 54' may still remain free of any cracks or fractures.

Conventional optimized stem designs typically allow up to, e.g., 5% diameter expansion from nominal deployment diameter, where most conventional stent designs allow for an expansion ranging from about 2% to 4%, while remaining within the elastic strain of the ultra high molecular weight (UHM) PLLA. However, the stent design and configuration described herein may allow for up to, e.g., 80% expansion (change in diameter) beyond nominal diameter, while remaining within the plastic deformation of the UHM PLLA without visible necking/narrowing of the ring elements. Furthermore, the stent design may allow up to, e.g., 250% expansion (change in diameter) beyond nominal diameter, without noticeable fracture as compared to a 35% expansion for conventional stents as illustrated in the comparative side views of FIGS. 10A and 10B.

Figure 10A:
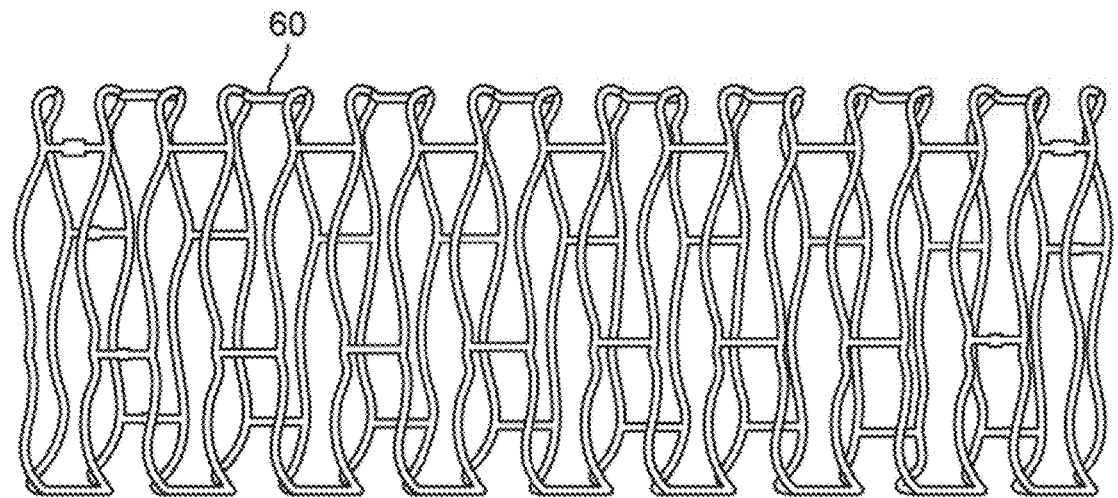
FIGS. 10A and 10B illustrate, respectively, comparative side views of a high molecular weight stent scaffold and a conventional low molecular weight stent scaffold to show the differences in expansion without fractures or cracking.
Figure 10B:
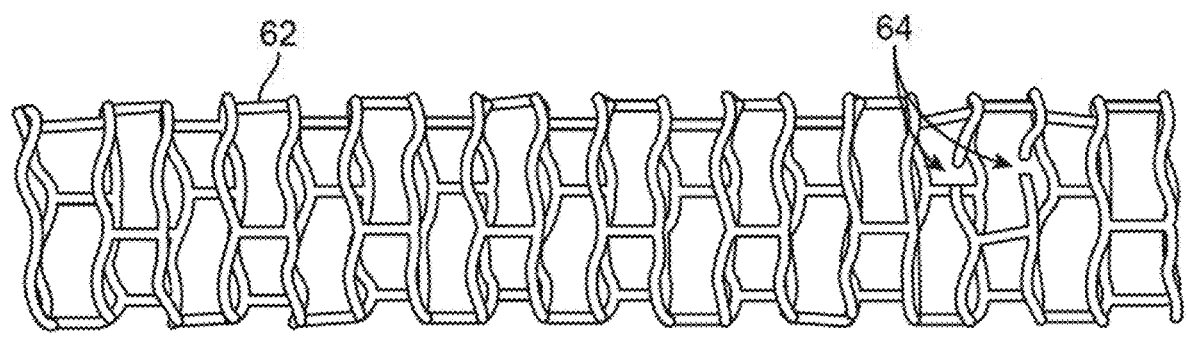

FIGS. 10A and 10B illustrate, respectively, comparative side views of a high molecular weight stem scaffold and a conventional low molecular weight stent scaffold to show the differences in expansion without fractures or cracking. FIG. 10A illustrates an example of a stem scaffold 60, fabricated as described herein, that had a pre-deployed dimension of 2.5 mm×18 mm expanded to 7.8 mm in diameter. This expansion is over 200% above its nominal diameter with no fractures or cracking. The stent design either increases or retains its radial force at nominal diameter throughout the range of expansion beyond nominal diameter due not only to strain recovery and elastic deformation but due also to the design configuration of the stem. On the other hand, FIG. 10B illustrates an example of a conventional bioabsorbable stent scaffold 62 (ABSORB GT1, Abbott Vascular Bioresorbable Vascular Scaffold. (BVS) System, Abbott Laboratories, Ill.) that had a pre-deployed dimension of 3.0 mm×18 mm expanded to 4 mm in diameter. This expansion is just 30% above its nominal diameter but with resulting fractures 64. A direct comparison between the scaffolds 60, 62 illustrates how the advantages of the present scaffold 60 result in a deployed diameter which is significantly greater than a conventional scaffold 62.

While the scaffold 60 has a shape memory effect imparted into the scaffold 60 during its fabrication, the increase in its radial strength is not due to this shape memory effect but rather due to the resiliency and strain recovery of the molecular chains forming the scaffold 60 as the diameter of the scaffold 60 does not increase after deployment despite the increase in its radial strength. In one embodiment, the scaffold design allows the struts to reorient themselves radially without causing significant strut elongation and thereby allows for increases in radial force of the scaffold due to increased geometric resistance of the scaffold to buckling. Such scaffold design would also have minimal increase in diametric recoil as long as the strain caused by the further expansion of the scaffold remains above tensile strain at yield and below strain causing strut elongation. In another embodiment, the scaffold design may be selected to minimize diametric recoil upon deployment whereupon expansion of the scaffold at deployment, the scaffold's polymer remains above tensile strain at yield and below strain causing strut elongation.

The scaffold design contains the stress and strain in strategic locations of the scaffold where diametric contraction or expansion is translated as relative angular displacement of struts. Diametric contraction or expansion, for example, can occur when the scaffold is crimped, expanded at deployment, or over-expanded at deployment. The scaffold design contains the stress and strain in the peaks and valleys of the scaffold and the angular arrangement of the struts is designed to allow a finite amount of over-expansion beyond the original intended diameter. Any expansion beyond the predetermined level may cause strut elongation, reduced radial force, increased diametric recoil, and decreased structural integrity and fatigue life. Solution casting a stem scaffold having such design characteristics provides another way of optimizing the stent scaffold of the invention.

In yet another embodiment, the scaffold, e.g., having a pre-deployed 3.80 mm REV 9 diameter, may have a tensile strain at yield within a range of, e.g., 3% to 4%, in one or more of the following conditions: crimping to onset of contact, crimping to catheter diameter inner diameter (ID), no crimping, axial extension of 6%, no crimping, axial contraction of 6%, crimping to implantation diameter and axial extension of 6%, crimping to implantation diameter and axial contraction of 6%, crimping to fixed lumen diameter and axial extension of 6%, and crimping to fixed lumen diameter and axial contraction of 6%.

In this example, the 3.8 mm REV 9 diameter design is an interconnected ring design where ring elements are connected with struts. Each of the struts join the peaks of one ring to the valley of an adjacent ring. A ring is comprised of twelve segments that are arranged in alternating angles. The ring elements have a width of 178 µm and the connecting struts are 117 µm wide and the rings are arranged in 1 mm increments. The resulting strain values of a non-linear finite element analysis of the scaffold is shown in FIG. 10C.

In yet another embodiment, a scaffold, e.g., having a pre-deployed 3.94 mm REV 13 diameter, may have a tensile strain at yield within a range of, e.g., 3% to 4%, in one or more of the following conditions: crimping to diameter just prior to onset of self-contact, crimping to an outside diameter of 1.1 mm, crimping to an outside diameter of 1.2 mm, no crimping and simultaneous axial contraction 6%, no crimping and simultaneous axial extension 6%, 15% crimping and simultaneous axial contraction 6%, 15% crimping and simultaneous axial extension 6%, 11% crimping and simultaneous axial contraction 6%, and 11% crimping and simultaneous axial extension 6%.

In another example, the 3.94 mm REV 13 diameter design is an interconnected ring design where ring elements are connected with struts. Each of the struts join the peaks of one ring to the valley of an adjacent ring. A ring is comprised of twelve segments that are arranged in alternating angles. The ring elements have width of 190 µm and the connecting struts are 132 µm wide and the rings are arranged in 1.1 mm increments. The resulting strain values of a non-linear finite element analysis of the scaffold is shown in FIG. 10D.

In yet another embodiment, a scaffold, e.g., having a pre-deployed 4.0 mm REV 23 diameter, may have a tensile strain at yield within a range of, e.g., 3% to 4%, in one or more of the following conditions: crimping to a diameter just prior to onset of self-contact, crimping to an outside diameter of 1.2 mm, crimping to an outside diameter of 1.0 mm, mild crimping and simultaneous axial contraction 6%, mild crimping and simultaneous axial extension 6%, aggressive crimping and simultaneous axial contraction 6%, aggressive crimping and simultaneous axial extension 6%.

In yet another example, the 4.0 mm REV 23 diameter design is an interconnected ring design where ring elements are connected with struts. Each of the struts join the peaks of one ring to the valley of an adjacent ring. A ring is comprised of twelve segments that are arranged in alternating angles. The ring elements have width of 185 µm and the connecting struts are 142 µm wide and the rings are arranged in 1.2 mm increments. The resulting strain values of a non-linear finite element analysis of the scaffold is shown in FIG. 10E.

Figure 11:
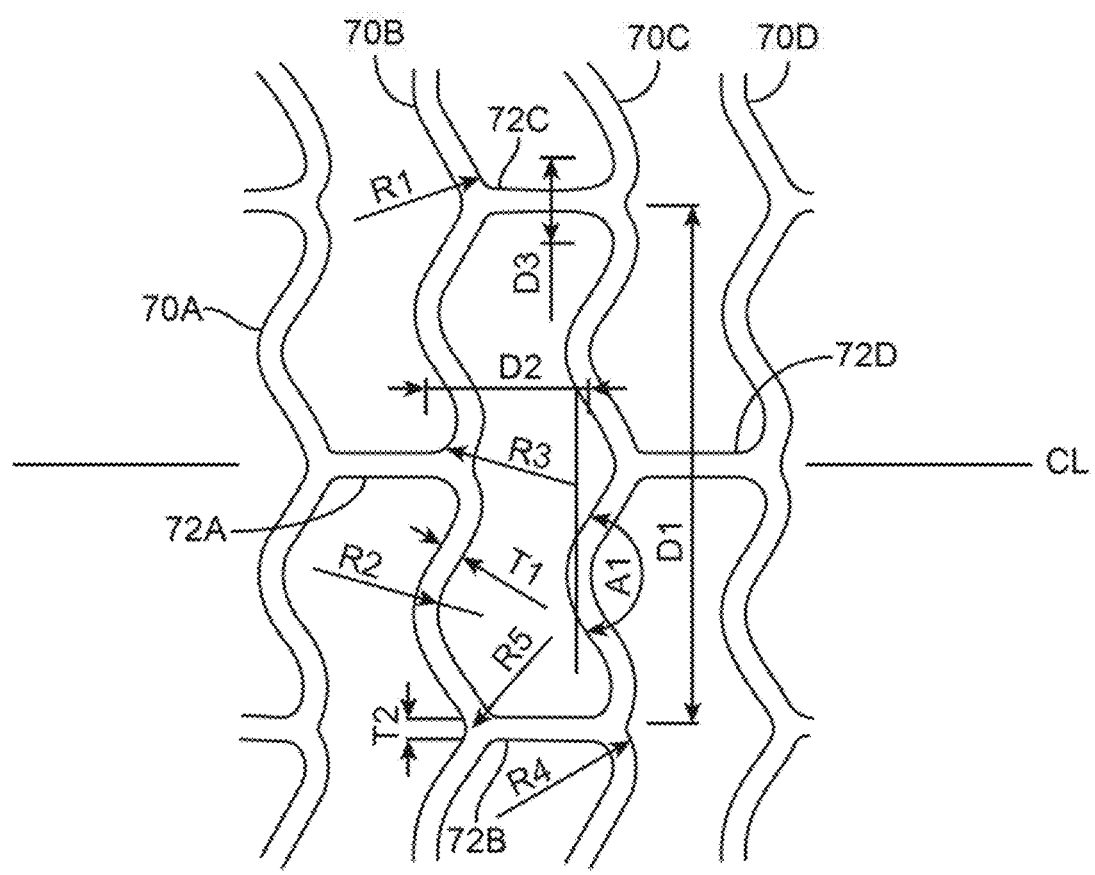
FIG. 11 illustrates an example of a stem pattern splayed about a centerline in its expanded configuration in detail in which the stent scaffold design is optimized to take advantage of the inherent material properties of the formed polymeric substrate.

FIG. 11 shows an example of a stent pattern splayed about a centerline in its expanded configuration in detail in which the stein scaffold design is optimized to take advantage of the inherent material properties of the formed polymeric substrate. The stem pattern shows one or more undulating circumferential support element 70, e.g., six support elements 70, which are similarly connected by one or more linking or coupling elements 72. In this example, two linking or coupling elements 72 which are apposed to one another along a circumference of support element 70 may connect or attach adjacent support elements 70 to one another. Each adjacent support element 70 may be coupled via the linking or coupling elements 72 aligned in an alternating pattern to provide the overall stem with sufficient flexibility along its length.

The splayed view of FIG. 11 illustrates the stent scaffold pattern in its expanded configuration in further detail. The unique processing methods (as described herein) are just another factor utilized to ultimately form the substrate to exhibit particular mechanical characteristics. The various processing methods and apparatus which may be utilized in forming the stems are described herein and are further described in the following: U.S. Pat. Nos. 8,206,635; 8,206,636; U.S. patent application Ser. No. 13/476,853 filed May 21, 2012 (U.S. Pub. 2012/0232643 A1); and U.S. patent application Ser. No. 12/541,095 filed Aug. 13, 2009 (U.S. Pub. 2010/0042202 A1), each of which is incorporated herein by reference in its entirety and for any purpose herein.

The stem of the invention is bioabsorbable while maintaining desirable mechanical properties when in use during deployment or when implanted within a patient body. The stem may be formed to have a wall thickness of, e.g., 80 µm, 90 µm, 120 µm, or 150 µm, or ranging anywhere between, e.g., 70 µm to 200 µm. In the case of a stent formed to have a wall thickness of 150 µm specific stent dimensions combined with the properties of the polymer may provide for significant mechanical behaviors such as radial strength, recoil, and stem retention.

For instance, a polymeric stem formed accordingly (as described herein) and having a wall thickness of 20 µm to 1 mm, e.g., 150 µm, with a stem length of 6 mm to 300 mm, e.g., 18 mm, may be formed to have an approximate surface area of 3 $mm^2$ to 3000 $mm^2$, e.g., 36.2 $mm^2$, over the outer surface of the stent at its outer diameter. The approximate total surface area of the stem accordingly may be 20 $mm^2$ to 12,000 $mm^2$, e.g., 139 $mm^2$.

For a stent embodiment having a wall thickness of 120 µm, such a stent may have the same or slightly different dimensions from those shown in particular areas to compensate for the reduction of wall thickness while maintaining particular mechanical properties. For stem embodiments having a wall thickness of 80 µm or 90 µm (or ranging in-between), the dimensions from those shown may also be the same or slightly different to compensate for differences in the reduction of wall thickness.

A stent may be formed to have the 150 µm wall thickness and 18 mm length formed from the polymeric substrate described herein. Accordingly, such a stem may be formed having multiple circumferential support elements 70 with linking or coupling elements 72 which extend between adjacent support elements 70 in an alternating pattern. An exemplary sub-set of the multiple circumferential support elements 70 and linking or coupling elements 72 are shown to illustrate particular stem dimensions.

The stent pattern illustrates the stein splayed about a centerline CL extending longitudinally relative to the stent. Several exemplary circumferential support elements 70A, 708, 70C, 70D are shown with the linking or coupling elements such as coupling element 72A connecting support element 70A and 708, coupling elements 72B and 72C connecting support elements 70B and 70C, and coupling element 729 connecting support element 70C and 70D. Each of the circumferential support elements may be formed to have a width of T1 (0.0005 in. to 0.1 in., e.g., 0.006 in.) while each of the coupling elements may be formed to have a width of T2 (0.0005 in. to 0.08 in., e.g., 0.005 in.) extending between the circumferential support elements, as shown.

The coupling elements may be aligned parallel relative to one another and parallel relative to the centerline CL of the stem. The coupling elements may also be spaced apart from one another at a distance of D1 (0.004 in, to 1.5 in., e.g., 0.136 in.) as measured when the stent is splayed flat or as measured circumferentially when the stem is normally deployed and expanded for implantation (shown as the splayed distance or circumferential distance between coupling elements 72B and 72C). The coupling elements may also be formed to have a length which spaces the adjacent circumferential support elements at a distance of 92 (0.004 in. to 1.5 in., e.g., 0.040 in.) from one another (shown as the longitudinal distance between support elements 70B and 70C).

Each of the circumferential support elements may be formed to have a sinusoidal or undulating wave pattern which is aligned adjacent to one another about the centerline CL such that a coupling element extends from a trough of one support element (e.g., support element 70A) to a trough of an adjacent support element (e.g., support element 70B). The proximal portion of the trough of the support element where the coupling element extends may form a radius R1 (0.0001 in. to 0.75 in., e.g., 0.012 in.) while the crest of the support element may also form a radius R2 (0.0005 in, to 0.5 in., e.g., 0.012 in.), as shown along support element 70B, and an angle A1 (15 degrees to 179 degrees, e.g., 120 degrees) formed between the adjacent portions of the support element.

Where the coupling element extends proximally from a first support element, the coupling element may simply project from the trough but where the coupling element joins with the adjacent support element, the trough may form a radius R4 (0.0001 in. to 0.75 in., e.g., 0.008 in.) along a proximal portion where the elements are joined as well as along a distal portion of the trough which curves distally to join with the coupling element. This may be seen, e.g., where coupling element 72B extends longitudinally proximal from the support element 70B forming a radius R5 (0.0001 in. to 0.75 in., e.g., 0.005 in.) as shown between support element 70B and coupling element 72B. The coupling element 72A projects proximally from the trough of support element 70A and joins with the corresponding trough of support element 70B where the trough forms a distally curved radius R3 (0.0001 in. to 0.75 in e.g., 0.006 in.). The proximal portion of the trough may accordingly define a distally curved radius R3 in-between proximally curved radii R4. The distance between the proximally curved radii R4 on both sides of the coupling element defines a distance D3 (0.0005 in. to 0.75 in., e.g., 0.022 in.).

With these stein dimensions formed from the polymeric substrate described herein, the combination enables such a stent to have particularly desirable mechanical properties. For instance, such a stem may exhibit a radial strength of between 1.0-1.5 N/mm with a recoil of 2%-5% and a stem retention of 0.5-1.5 N. Additionally, the fatigue life of the stent may also be improved significantly, e.g., an increase of up to 150 million cycles (or 1500%) over conventional polymeric stents. These values (e.g., radial strength, recoil, stem retention, fatigue life, molecular weight, etc.) are expressly applicable to any of the stein embodiments described herein having different wall thicknesses or other dimensions. For instance, these values are applicable for stent embodiments having a wall thickness of, e.g., 80 µm, 90 µm, 120 µm, or 150 µm, or ranging anywhere between, e.g., 70 µm to 200 µm.

Effects of Tensile Strain at Yield on Radial Strength Recovery after Deployment

Tensile strain at yield is another factor that effects radial strength recovery after deployment. Not only is the scaffold designed to contain the stress and strain in strategic locations of file scaffold, the properties of the polymer can be controlled in order to effect radial strength of the scaffold at deployment into a saline environment and a temperature of, e.g., at least 37° C. Such properties of the polymer that can be controlled during the manufacture of the scaffold in a dip-coated scaffold are the elongation break, modulus, and tensile strain at yield. In one embodiment, the tensile strain at yield of the polymer used to manufacture the scaffold is kept within a range of e.g., 3% to 4%, to allow for the propensity of the tube to regain strength once the tube is exposed to a temperature of, e.g., at least 37° C., in a saline condition. In this embodiment, the scaffold has the ability to recover pre-crimp and pre-expansion radial strength when the scaffold is deployed into a saline environment at a temperature of, e.g., at least 37° C. and below $T_g$ of the polymer. In one embodiment of a PLLA 8.28, 30% to 70% of the acute radial strength of the scaffold is recovered when deployed in saline condition at a temperature of at least 37° C. and below $T_g$ of the polymer.

The radial force increase after deployment of the scaffold is not due to creep or shape memory of a polymer. On the contrary, the radial force recovery upon deployment over a period of time and temperature is due to strain recovery. Once a scaffold is deployed, compression load is always applied to a scaffold by the vessel pulsating. There is a damage of the polymer chains which are stretched, thereby opening the network of polymers. The recovery depends on how strong the interactions of the polymer chains are with one another, which is a time-temperature phenomenon.

When the tube of a tight network of polymer chains is caused to deform, the polymer chain network is opened up, and upon exposure to elevated temperature in a saline environment, the polymer chain network at least partially reverts back to the original polymer chain network that the polymer had prior to being deformed. In the present case, the scaffold undergoes deformation when it was crimped and is later expanded when it was deployed. Due to the interaction of the polymer chains of the high molecular weight polymer, the polymer chains reorient themselves within the network to essentially recapture some of the radial force that was lost upon deformation or crimping.

One of the factors that influence the propensity of the polymer chain network to recover to its original polymer chain network at least partially is a polymer's molecular weight. The higher the molecular weight, the longer the polymer chains, the higher amount of force, and the higher the % efficiency of the scaffolds propensity to recover at least part of the scaffold's original radial strength prior to the crimping and expansion of the stent scaffold. The propensity for the scaffold to be able to recover its radial strength can be measured with tensile strain at yield (%). FIG. 12 shows a table with examples of stem scaffolds which have been fabricated to the dimensions indicated and by methods described herein to illustrate the various material property parameters achieved. PLLA 8.28's tensile strain at yield (%) is indicated in FIG. 12. Depending on the polymer's molecular weight, the longer the length, the higher the amount of force, and the higher the percent efficiency of the scaffolds radials strength recovery. The network is able to recapture some of the radial force that was lost upon deformation, crimping, and/or expansion because of the high molecular weight polymer's ability to reorient itself within the network to essentially recover its original polymer chain network when the polymer is exposed to elevated temperature in saline conditions. Examples of stent scaffolds fabricated to the dimensions as shown and by using the methods described herein are shown in the table in FIG. 12 to illustrate the various parameters of material properties achieved. The examples use a 100% 8.2 PLLA scaffold. For instance, for a scaffold having an average 5.10 mm outer diameter with an average 0.176 mm wall thickness, the following average values were achieved: 80.67 MPa, tensile strain at yield; 3.67%, tensile strain at yield; 205.32 MPa, tensile load at break; 75.39 MPa, tensile strain at break; 109.48%, tensile strain at break; and 2708.90 MPa, elastic modulus.

Effects of Yield Division on Radial Strength

Figure 13:
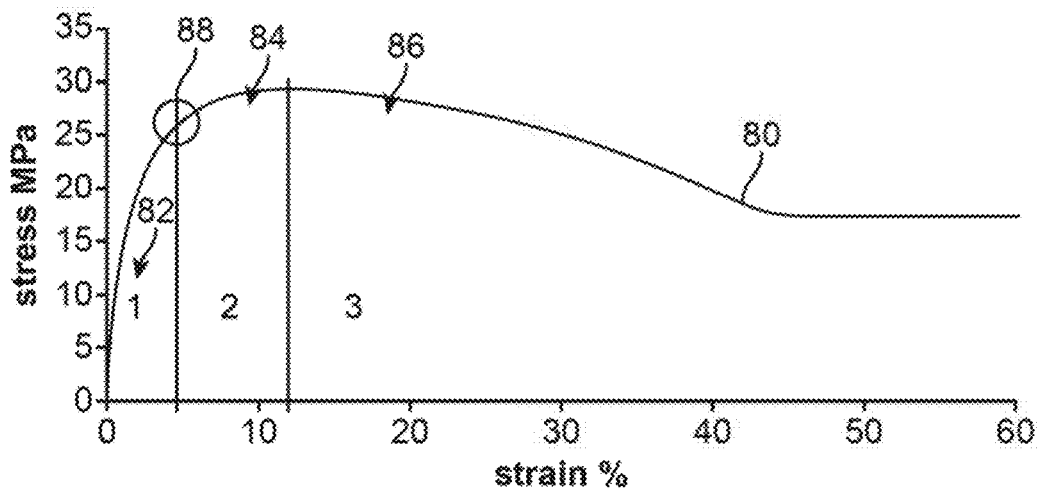
FIG. 13 illustrates a stress-strain curve of a stem scaffold fabricated accordingly as described herein and the different phases of material strain that the scaffold undergoes when subjected to the stress shown.

FIG. 13 illustrates a stress-strain curve 80 of a stent scaffold fabricated accordingly as described herein and the different phases of material strain that the scaffold undergoes when subjected to the stress shown. The stress-strain curve 80 is shown with three different regions to illustrate the different phases of material strain that the scaffold undergoes when subjected to the stress shown. The first region 82 corresponds to viscoelastic (recoverable) deformation, which is the elastic component of the polymer. The second region 84 starts with the plastic point 88, shown circled, of the material, which comprises the plastic component of the polymer. Plastic deformations become significant through craze formations and/or homogenous flow (shear bands). The third region 86 corresponds to the formation of a necking region in the specimen, or 100% plastic component, which is a deformation that is dominated by a massive homogenous flow in the drawing regions.

As yield division effects radial strength of the scaffold, much of the yield division may be attributable to the relatively high molecular weight of the polymer, as well as the scaffold's geometric configuration, as described herein. When deformation is caused by crimping, and deployment or expansion, there is a predictable elastic component of the scaffold that is able to be recovered due to the high molecular weight of the scaffold as well as the geometry of the scaffold. Even if the elastic component of the scaffold is not able to be measured, the geometry of the scaffold also reacts to the load. The load is complex due in pan to an axial component to load. When the scaffold is compressed, the diameter of the scaffold reduces and the length increases. A polymer that moves in a pulsatile motion also moves in an axial motion. In other words, every pulsatile motion has an axial component. Thus, the scaffold moves axially as well as in a pulsatile motion. Because of this multiple component part of this load, it can be difficult to predict the behavior of the scaffold after deformation because the stress/strain curve is not linear. Pulsatile motion makes fatigue life more difficult to predict and so the axial fatigue on the scaffold may be aggressively modeled as fatigue may increase over time. In one embodiment, the acute fatigue is lessened upon deployment of the scaffold and radial strength increases with time.

As there is a difference between viscoelastic strain (recoverable) and plastic strain (non-recoverable), it is desirable to know at what strains and stresses the material fails when designing scaffolds. Plastics are dramatically different from metals in their stress-strain behavior. Unlike metals, plastics undergo significant strain prior to yielding, often as high as 5% to 7% strain. A significant portion of this strain can be plastic in nature, which causes irreversible damage and it is generally imprudent to assume that the material is stable up to its yield point; hence, it is desirable to determine the recoverable strain and plastic strain values. Secondly, it is desirable to know at what strain and stress level these deformations start to be significant. Thirdly, simulation of damage accumulation and recovery after loading are generally not feasible unless the relationship between recoverable strain and plastic strain is known. The elastic component of deformation is recoverable.

Figure 14:
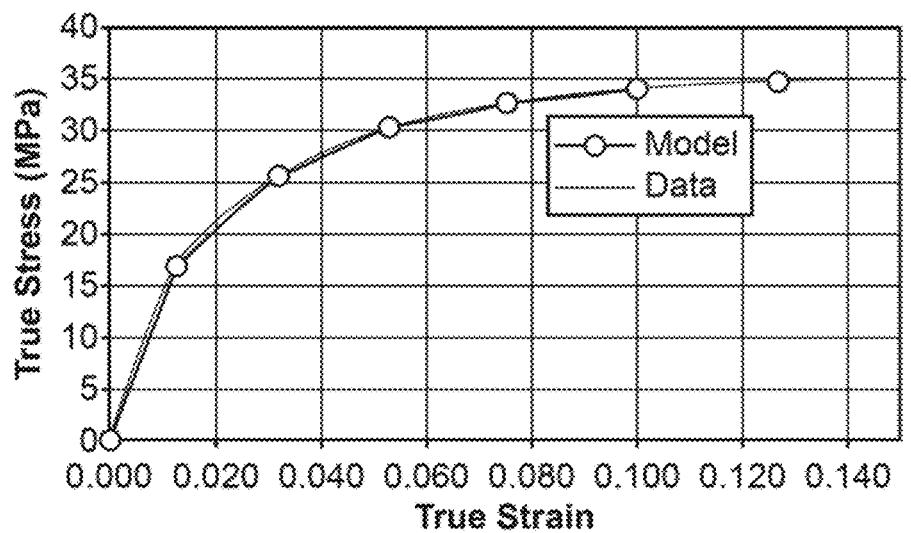
FIG. 14 illustrates a chart of a stress-strain curve comparing values between an elastic-plastic material model implemented for a polypropylene plastic and actual test data.

When the scaffold is deformed, the combination of geometry and the material properties of the scaffold is tuned to give it an elastic component to that deformation. The elastic component of the polymer in the scaffold is a factor in determining how much radial force will be recovered upon deployment. Elasticity of a polymer for scaffold purposes is generally needed for compliance and the elastic deformation must be balanced with plastic deformation, which is needed to set the intended scaffold diameter of the tube for maintaining luminal patency for keeping the vessel opening. A common mechanical test for plastics is the tensile test, as noted above, where a specimen is stretched at a constant speed while and the forces are recorded. A stress-strain curve can then be derived and often the yield point, which is the maximum of the stress strain curve, is generally assumed to be synonymous with the onset of plastic deformation. However, it has been shown that plastic flow actually starts before this yield point and the maximum on the stress-strain curve actually corresponds to the point where the specimen becomes unstable and forms a neck. The stress-strain curve can then be decomposed in the following regions shown in FIG. 13. By nature, plastics exhibit non-linear elasticity as seen in FIG. 13 there is often a lack of a linear portion to the initial stress-strain curve. Instead, the tangent modulus is seen to steadily decrease with increasing strain all the way to the yield point. At the plastic point 88, the plastic begins to take on irrecoverable plastic, strain and such behavior plays havoc with the classical elastic-plastic material model because it is often incorrect to use a secant modulus to describe the elastic stress-strain relationship below the plastic point. While such a model has some applicability for the simulation of large deformations, it will show the material to be soft at low strains as seen in FIG. 14 which compares the stress-strain values between an elastic-plastic material model implemented for a polypropylene plastic and actual test data.

Lastly, the issue of viscoelasticity cannot be ignored. Even in the so-called elastic region, deformation recovery of a plastic is not instantaneous. Rather, the plastic returns to its original state after a period of time that is dependent on its viscoelastic characteristics, as described by a stress-recovery curve. This time dependency is well characterized by viscoelastic experiments and can be modeled well in high end computer aided engineering (CAE) applications via a Prony series. However, viscoelastic theory implemented in most CAE programs is a linear theory and therefore unsuitable for large-strains where the viscoelastic behavior itself becomes non-linear. As permanent irrecoverable plastic strain occurs, the material itself is changed and now has a new characteristic that is entirely different from the original material. Accordingly, linear viscoelastic models will not work beyond the plastic point. This points clearly to the importance of knowing the plastic point and using it as a fundamental basis for placing stress limits on a design. The plastic point could potentially have implications related to endurance life and strain recovery.

The components to deformation of a polymer make polymer technology very unpredictable. Several factors should be considered in order to manufacture a scaffold that is able to perform in a predictable manner when exposed to an elevated temperature and a saline environment such as in a patient. For this reason, the polymeric scaffolds also behave very differently from metal stems. In one embodiment, the viscoelastic properties of a scaffold are controlled in order to control radial strength recovery upon deployment of the scaffold. Every polymer has viscoelastic properties. When a polymer responds to an external load or deformation, there is a viscous and elastic component to that deformation. The viscous component never recovers, but the elastic component of the deformation can recover upon exposure to saline conditions and elevated temperature as well as enough time.

Tensile strain at yield (%) is a property of polymers and can be partially recoverable so long as there is an elastic component to the polymer. For example, if a polymer has a tensile strain at yield of 3.6%, and 2.6% is recoverable and 1.0% is not recoverable in body temperature at saline conditions, a certain portion of the tensile strain at yield is recovered. When the yield point is reached, a certain portion of yield is recoverable. Using this strain recover theory, the scaffold can be designed that upon crimping or deformation, certain parts of the scaffold having high deformation go through this yield. When yield at scaffold deformation or crimping occurs, some yield has not reached plastic deformation. More of strain storage capacity is present and is stored in the scaffold such that when the scaffold is expanded upon deployment in the patient, the scaffold reverts back to a pre-deformation state of strain. In essence, the elastic component of deformation is stored in the deformed scaffold such that it is released upon deployment, recovering its radial strength.

The percent deformation that is attributable to the elastic component versus viscous component plays a role in how much the scaffold can recover its radial force after deployment of the scaffold in a saline environment at body temperature. If the viscoelastic ratio stays within a certain parameter of the strain-stress distribution, significant strain recovery, and thus radial force will be regained or recovered over time. The radial force recovery is significant in the scaffold shown in FIG. 11 due to relatively higher elastic deformation being present in the scaffold's struts and elastic deformation by its nature is recoverable at 37° C. in saline condition.

In view of this, a method of designing a stem scaffold is available based on stress or strain distribution when the scaffold is crimped onto the catheter and later deployed or expanded into the lumen of a patient. The scaffold may be designed to produce a certain amount of strain upon deformation when crimping and later deploying or expanding the scaffold. The scaffold is crimped down to the diameter of the catheter, and because the design of the scaffold was tested, it is known to produce a certain amount of strain upon deformation. For example, the scaffold strut can produce, e.g., a 154% strain percentage, when crimped down to the diameter of the catheter. If the scaffold is instead axially pulled, another strain percentage may be produced in the scaffold's strut.

In one example, a stein scaffold was tested and the strain distribution was measured at various compressing and axial deformations. If a 3.2 mm scaffold strut stays within a certain tensile strain percentage, the scaffold will exhibit a certain strain capacity. Thus, a scaffold fabricated as described herein will have a certain elastic versus viscous deformation at a given design. Upon elevated temperatures in saline conditions, the scaffold recovers radial strength at a given time. In one embodiment, at a given design of the scaffold, the tensile strain at yield is kept at a value of, e.g., 3% to 4%, in order to ensure radial force recovery of at least 30%. In another embodiment, a design of the scaffold may be selected such that fatigue is optimal and tensile strain at yield is selected from, e.g., 3% to 4%, to impart a radial strength recovery of at least 30%.

Fracture resistance is evaluated by applying multi-modal cyclic loads to the scaffolds. The cyclic loads are similar to conditions present in physiological environments but with 50-100% greater amplitude to highlight mechanical properties of the scaffolds. Fatigue testing proves that the scaffold of the invention outperforms the conventional scaffolds post deployment because there is less risk of chronic dismantlement which leads to thrombosis. Because the high molecular weight polymer that is used to solution cast the scaffold in the invention, the ductility of the scaffold makes for a more robust scaffold for a significant period of time post deployment. Therefore, many factors come into play including an increase in radial force that provides for a more robust scaffold having better chronic performance at least 7 months after deployment, and therefore less risk of chronic dismantlement which leads to late thrombosis in scaffolds of the prior art.

Figure 15:
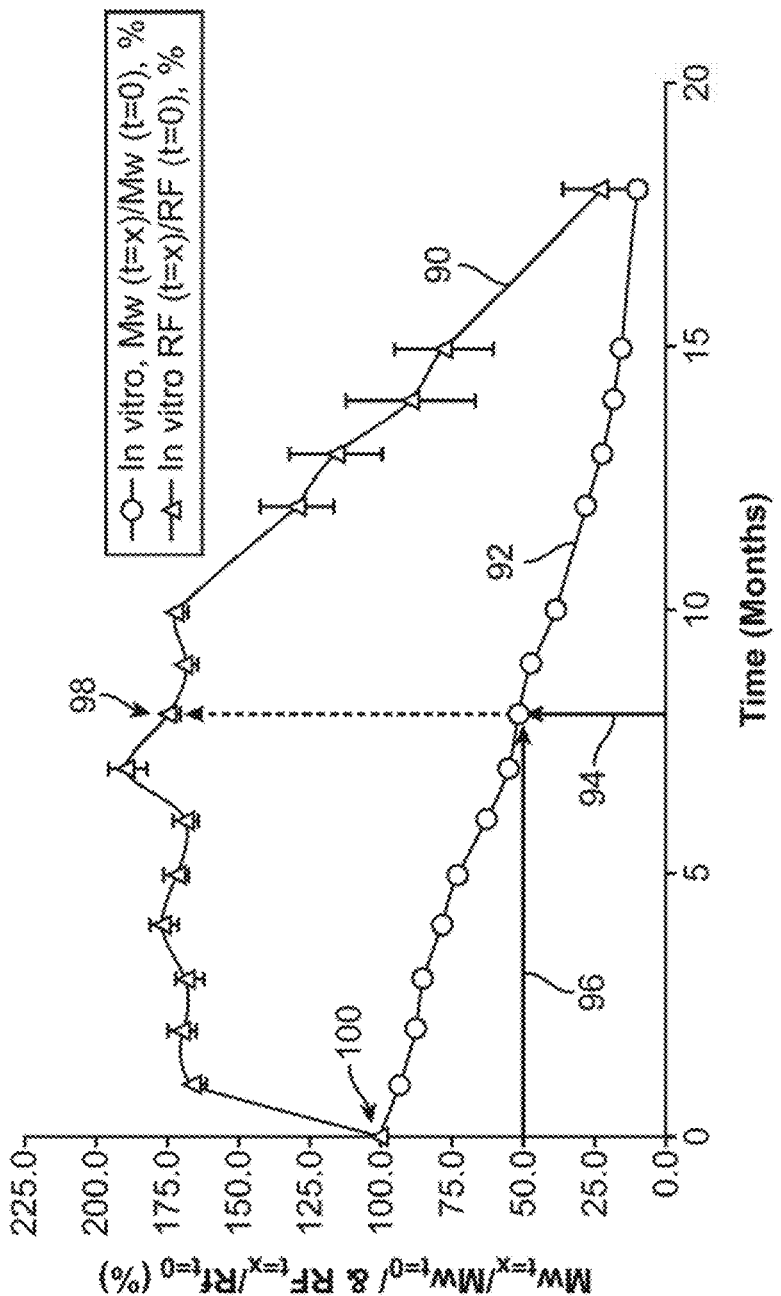
FIG. 15 illustrates a chart showing a ratio of the radial strength and the molecular weight of a PLLA scaffold as a function of time.

Turning now to FIG. 15, a graph illustrates a ratio of the radial strength and the molecular weight of a MLA scaffold made at 150 microns as a function of time. The scaffold's percentage of radial strength 90 ($RF_{t=x}/RF_{t=0}$) is shown to increase immediately after implantation and throughout the first month of implantation. By maintaining the tensile strain at yield of the scaffold at 3% to 4%, the tensile strain at yield can be used to guide the scaffold design to ensure that there will be a certain strain recovery, which translates into radial force recovery upon deployment of the scaffold in a patient. The radial force recovery after deployment occurs for a period of several months, as shown, up to 7 months 94 after deployment. This radial force after a period of several months is the chronic radial force 98 of the scaffold, and is higher than the acute radial force 100 of the scaffold, which is the radial force of the scaffold upon deployment.

The scaffold design is therefore dictated by the tensile strain at yield percentage. The tensile strain at yield percentage provides for a scaffold that will perform upon deployment to an acceptable level of recovery of radial force. If strut design is fabricated to have a tensile strain at yield between 3% to 4%, then the struts will exhibit a certain radial strength recovery upon deployment. In one embodiment, a method of manufacturing a scaffold is provided having a design that provides a certain tensile strain at yield of 3% to 4%, wherein the radial force of the scaffold recovers to at least 30% of the radial force prior to deformation (crimping and deployment expansion).

Contrary to the prior art, once the scaffold is deployed, the radial strength of the scaffold recovers much of the radial strength of the scaffold prior to crimping and deployment. As illustrated in FIG. 15, the radial strength increases to almost double that at the time of deployment. Thus, the radial strength is not only sustained overtime, but also is recovered to at least 30%.

Without being limited by theory, it is believed that this recovered chronic radial strength is due to the elastic deformation of the polymer that is recoverable upon elevated temperature and a saline condition. This radial strength of the scaffold is reduced upon deformation at crimping but is also stored in the scaffold such that upon deployment or expansion of the scaffold, the radial strength is at least partially released or recovered. Once the scaffold is expanded upon deployment in a patient, the polymer chains have the ability for realignment of the polymer chain to their original configuration. Thus, the radial strength is retained in the scaffold when in a deformed or crimped state, and only later releases the energy of the scaffold when the scaffold is expanded upon deployment in the patient. In time, the scaffold is able to recover at least 30% of the radial force that was stored in the scaffold when the scaffold was crimped onto a catheter.

As further illustrated in FIG. 15, the sustainability of radial strength over time versus the polymer degradation profile 92 is also shown. Without being limited by theory, it is believed that upon expansion or deployment, the polymer recovers some of the radial strength that it lost upon crimping and expansion at deployment. A portion of the elastic radial strength that is lost when the scaffold is crimped is recovered upon expansion at deployment in a saline environment at body temperature. The stored radial strength is recovered after deployment over several months. As further illustrated in FIG. 15, the recovery of the radial strength 90 is seen to be relatively quick after deployment in the first month and then tapers off in the following months. The polymer chains of a high molecular weight polymer of the scaffold design are able to realign themselves as they were prior to being crimped. Although the scaffold's radial strength 90 is reduced upon crimping and deployment, the radial strength 90 is at least partially regained or recovered when the scaffold is deployed or expanded in a patient. The scaffolds ability to recover some of its original radial strength that it lost upon crimping and expansion is due to strain recovery of the polymer and polymer chain realignment upon exposure to body temperature and a saline condition. Thus, the radial force is stored in the crimped state, and later at least partially recovered when it is deployed or expanded.

Thus, radial force 90 of the scaffold increases as a function of time in the saline and elevated temperature of the patient. The degradation profile 92 of the polymer is hydrolysis or pH driven. There is a trigger condition that increases the radial strength of the scaffold, which is an increase in temperature in saline conditions. Because of the recoverable strain or elastic component of the scaffold's deformation, time and body temperature, polymer chains align themselves to pre-crimp and pre-expansion conditions in saline conditions. Upon strain recovery, the polymer repairs itself to almost the same radial strength it had pre-crimping and pre-expansion or deployment of the scaffold. In one embodiment, the scaffold increases the radial force from the time of deployment until a point after about 1 month of deployment by at least 30%. In one aspect of this embodiment, the radial force increases at least 20% from 7 months after deployment (chronic radial force) as compared to post deployment (acute radial force).

In a sense, the scaffold recovers its radial strength almost immediately after deployment. Internal molecules of the scaffold realize or repair the first crimp and expansion damage. In fact, there is no compromise of integrity for the duration of the year in the lumen because the radial force does not decrease below the scaffold's radial strength at deployment for at least about 6 months. Not only does the radial force increase over time post deployment, the ductility of the scaffold that is maintained over time due to the high molecular weight of the polymer provides for a more robust scaffold several months post deployment. The radial force and the ductility of the scaffold that is retained in the scaffolds original design makes for a better performing scaffold having better fatigue testing results, thereby providing a scaffold that resists fractures for a significant time post deployment. For example, in one embodiment, the radial force is recovered at least partially and the ductility of the scaffold is retained for a period of at least 7 months post deployment. Chronic dismantlement caused by early fractures at deployment is therefore avoided in the present invention because less fractures are caused upon expansion at deployment and at a later period of time, thereby prolonging dismantlement and significantly reducing the risk of late thrombosis as compared to prior art scaffolds that have late dismantlement caused by brittleness.

In addition to the radial force 90 and degradation profile 92 of the scaffold, the crystallinity and strain recovery; elastic component of the polymer may be examined. The regain of radial force is due to a completely different phenomenon from prior art scaffolds that may increase slightly in crystallinity at deployment. Conventional scaffolds that have been radially expanded by melt processes during its manufacturing may increase in crystallinity due to the polymer's absorption of water and their radial strength is strictly due to the amount of crystallinity of the polymer that has been induced by processes such as radial expansion. However, this increase in crystallinity of the conventional scaffold causes brittleness in the scaffold and results in fractures of the scaffold after implantation. These devices have low molecular weight and are usually sterilized by e-beam sterilization which reduce the molecular weight of the polymer even further. Deformation of the low molecular weight polymer of the conventional scaffold is a very viscous or plastic deformation, having little or no elastic deformation. Moreover, deformation of a conventional scaffold upon crimping, is mainly due to plastic or viscous deformation.

Figure 16A:
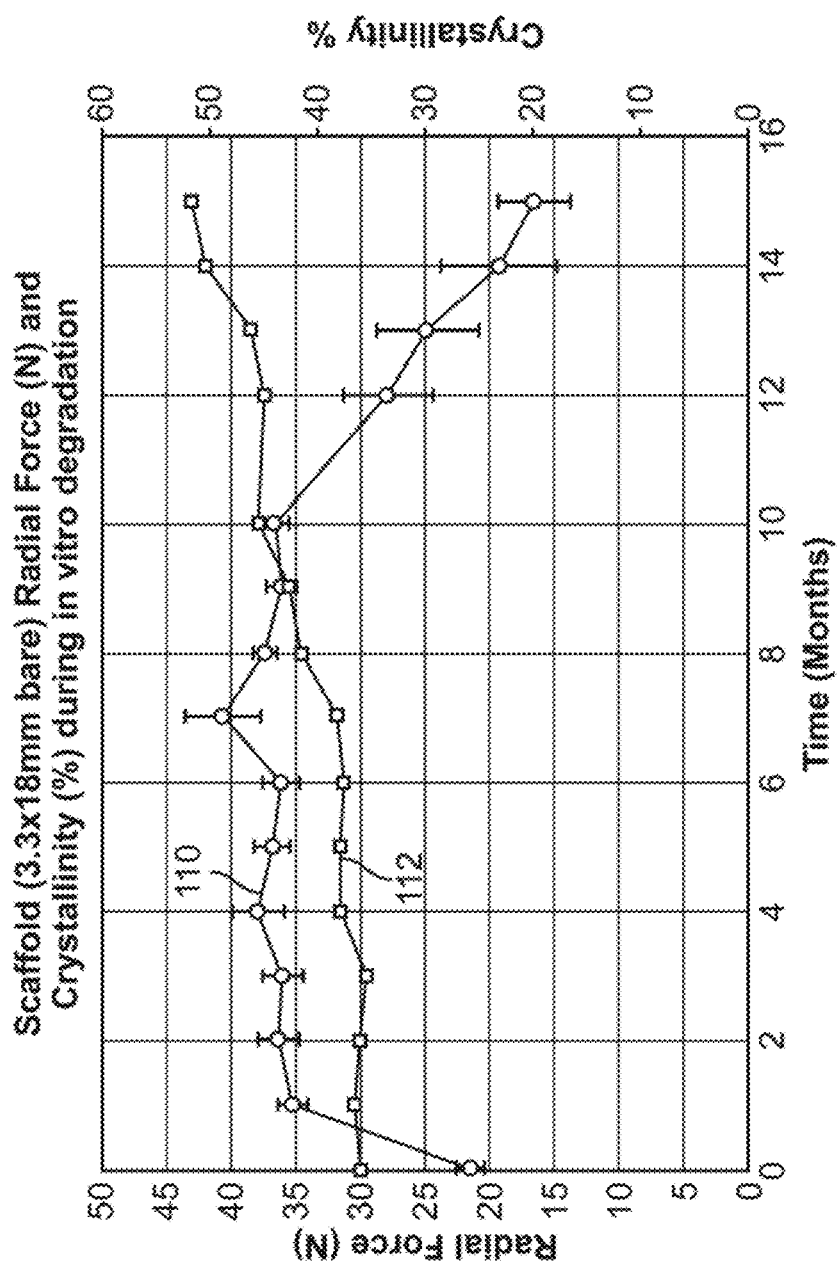
FIG. 16A illustrates a chart of the radial strength and crystallinity of a stem scaffold tracked over a period of time.

Comparatively, in FIG. 16A, the scaffold recovers its radial strength 110 within hours, and at most, within a few days, and continues to regain radial force over a period of, e.g., 7 months. FIG. 16A illustrates a chart of the radial strength 110 and crystallinity of a stent scaffold tracked over a period of time. The crystallinity 112 increase of the device is not more than 2% (30% to 32% from month 1 to month 7), so the immediate recovery of radial force is not attributable to the crystallinity. Thus, the percent of radial force recovery as well as the speed of radial force recovery show that the mechanical properties of the scaffold have very little to do with increase in crystallinity. A high molecular weight polymer subjected to 37° C. in saline conditions would take months to increase crystallinity to a point where radial force is increased to the same degree. Even at a high temperature of, e.g., 100° C. to 120° C., an increase of crystallinity that would be attributable to the percent of radial strength that is recovered would take an amount of time that is much longer than a few days. As shown in FIG. 16A, the radial force 110 of the scaffold begins to recover within days, so the radial strength recovery cannot be attributed to the crystallinity 112 increase within a few days. Yet, there is a spike of radial force 110 of the scaffold upon deployment.

If crystallinity were to increase to the degree of radial force increase as a function of time, hydrolysis would be onset earlier than desired, causing the scaffold to become brittle very quickly and decrease of molecular weight as well, thus becoming weak early after deployment. With conventional scaffolds, any radial force increase is generally due to crystallinity increase over time and this crystallinity increase is due to the scaffold having a low molecular weight polymer. Increase in crystallinity at deployment is not a desired effect in a lumen because a more brittle scaffold is formed upon increase in crystallinity in the lumen. The water seeps into the gaps between the chains in the amorphous regions and hydrolyzes the amorphous regions first, causing semi crystallization of the amorphous regions, which although is not the same effect as native crystallinity to the polymer, the amorphous regions are still becoming more brittle and crystallinity still increases in the scaffold.

Thus, although in the molecular weight decreases as function of time in FIG. 16A, there is a hydrolytic effect in the amorphous regions of the high molecular weight polymer scaffold which increases the crystallinity of the scaffold as a function of time. The radial force 110 increase as a function of time cannot be attributed to this slight increase of crystallinity 112. The radial force 110 increase is from about 35 N to 45 N from month 1 to month 7, which is a 75% increase in radial force. Hence, this increase in radial force at this level and at this ambient temperature within such a short period of time is due to more than crystallinity alone.

Crystallinity and fracture toughness have an inverse relationship. That is, the more crystallinity in a scaffold, the less fracture toughness in the scaffold. For this reason, the present scaffold having a crystallinity that is less than 50%, has a higher fracture toughness than the conventional scaffolds of higher crystallinity. At the point that the crystallinity is increasing, the radial force 110 decreases. The conventional scaffolds having aligned chains to keep crystallinity to a minimum and the conventional scaffold has a biased product to fracture toughness. Thus, to increase fracture toughness, oriented polymers in crystallinity with aligned chains keep crystallinity to a minimum level. Efficiency of radial strength recover is directly proportional to length of the polymer chains.

The increase of radial force in the scaffold of the present scaffold cannot be due to shape memory effect because the scaffold is deployed at a diameter which is the same diameter of the as formed substrate. The scaffold is not deployed at a diameter that is less than the as formed diameter to cause the shape memory effect. It should also be noted that the $T_g$ of PLLA is almost double the temperature of 37° C., which also shows that there is no shape memory effect at the low temperature of the body. For these reasons, the radial strength increase in the present scaffold is a function of strain recovery as opposed to shape memory effect of the polymer. The strain recovery realigns the polymer chains of the scaffold of the invention at a temperature that is at least 37° C. and below the $T_g$ of the polymer of the scaffold. The scaffold of the present invention has the ability to realign the polymer chains back to the original configuration at least partially without causing the shape of the scaffold to change or deform, in contrast to a shape memory polymers which are polymeric smart materials that have the ability to return from a. deformed state (temporary shape) to their original (permanent) shape induced by an external stimulus (trigger), such as temperature change. It is very clear in the present invention that the strain recovery is not due to a shape memory effect because the diameter of the scaffold as it is implanted is the same diameter of the lumen. In the case of shape memory polymeric scaffolds, the scaffold is deployed at a diameter that is smaller than the lumen, and the scaffold then imparts a shape memory effect and change in shape at a temperature of $T_g$ of the polymer in order to fill the lumen. In the present invention, at least in the embodiment of the scaffold of PLLA there is no shape memory effect in the lumen having a temperature of 37° C. because the shape memory effect requires that the temperature of the polymer be at least at $T_g$ which is much higher than 37° C.

Figure 16B:
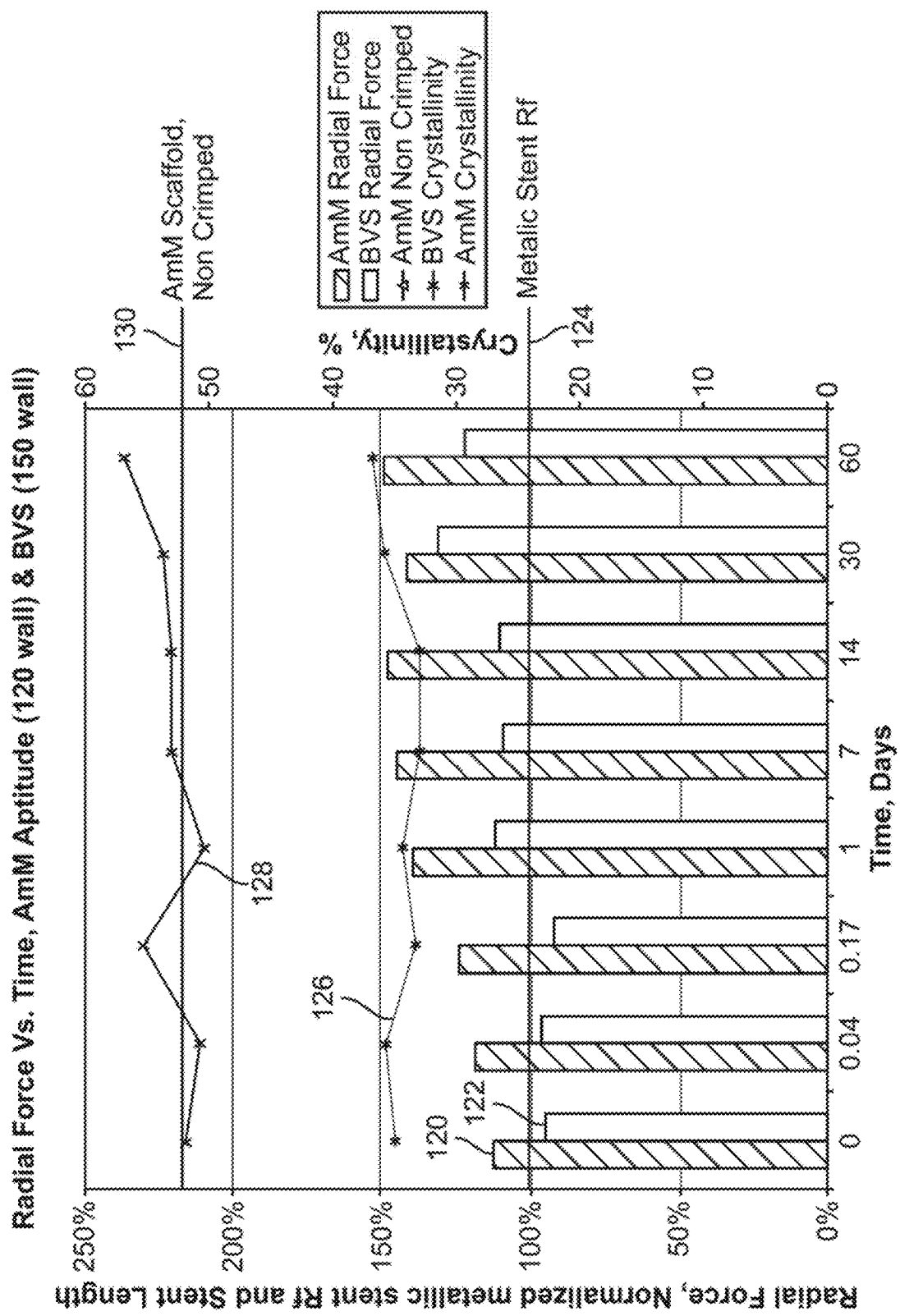
FIG. 16B illustrates a chart comparing the radial force and crystallinity of a stem scaffold fabricated accordingly as described herein against the radial force and crystallinity of a conventional stem scaffold.

Another example is illustrated in the chart shown in FIG. 16B. FIG. 16B illustrates a chart comparing the radial force and crystallinity of a stein scaffold 60 fabricated accordingly as described herein against the radial force and crystallinity of a conventional stein scaffold. FIG. 16B shows a comparison of radial force over time between a stent scaffold 60 having a 120 μm wall thickness fabricated according to the disclosure (as shown in FIG. 10A) and a conventional polymeric stem scaffold 62 having a 150 μm wall thickness (as shown FIG. 10B, ABSORB GT1, Abbott Vascular Bioresorbable Vascular Scaffold (BVS) System). Comparing the radial force 120 for the present stent scaffold 60 and the radial force 122 of the conventional scaffold 62 shows that over a period of time (60 days), the radial force increased for both although the radial force 120 of the present scaffold 60 was significantly greater than the conventional scaffold 62. The radial force 124 of a conventional metallic stent scaffold is shown for comparison which illustrates how this radial force 124 remains unchanged over the time period and the radial force 130 of a non-crimped stem scaffold 60 is also shown for comparison.

However, comparing the crystallinity 126 of the present scaffold 60 illustrates that its level is significantly below the crystallinity 128 of the convention scaffold 62, as discussed above. Hence, the present scaffold 60 is able to result in a significantly greater Example 1

In this example, a scaffold implant was mechanically crimped onto a rapid exchange (RX) balloon catheter delivery system. Finite element analysis (FEA) was used to characterize the scaffold in various crimped configurations under various compressive and extension loads to calculate the corresponding strain values. Due to the novel nature of the scaffold polymeric material and unique wall thickness, the results gathered from this evaluation are for characterization only. This analysis summarizes the strain values at critical points of the scaffold geometry and compares the FEA results for scaffolds having diameters ranging from about 3 mm to 4 mm. The FEA results demonstrated that strain in various configurations for each scaffold had similar results to one another. This is attributable to the unique and proprietary properties of the scaffold material and the unique scaffold wall thickness, as described herein.

Example 2

The FEA analysis was repeated for scaffolds which were coated with a drug (Sirolimus) and similarly having diameters ranging from about 3 mm to 4 mm. The sirolimus drug-coated coronary scaffold implant was mechanically crimped onto a RX balloon catheter delivery system and FEA was used to determine if the mechanical crimping has deformed the laser cut shape beyond the point of a reversible loss, potentially creating a failure when the balloon is inflated to deploy the scaffold. The resulting FEA strain analysis demonstrated that strain in various configurations for each scaffold demonstrated similar results to one another. Due to the unique properties of the scaffold material and the unique scaffold wall thickness. In conclusion, based on these data, the strain was acceptable for all the tested stent scaffolds.

Example 3

The FEA analysis was repeated for scaffolds which were coated with a drug (Sirolimus) and similarly having diameters ranging from about 3 mm to 4 mm. The sirolimus drug-coated coronary scaffold implant was again mechanically crimped onto a RX balloon catheter delivery system and FEA strain analysis was used to determine if the mechanical crimping had deformed the laser cut scaffold's shape beyond the point of a reversible loss, potentially creating a failure when the balloon is inflated to deploy the scaffold. This analysis summarizes the strain at critical points of the scaffold geometry and compares the values at different scaffold diameters.

The scaffold with a relatively smaller diameter and with no drug coating was tested extensively in five animal studies. In addition, eight of thirteen non-coated scaffolds were implanted in human patients. Each of these scaffolds have shown very favorable mechanical results. Since the primary mode of action is the scaffold mechanical strength, it is logical to compare the two devices with each other. The relatively larger diameter scaffolds compared favorably with the smaller diameter scaffolds thus verifying the strain being acceptable for the scaffolds described herein with respect to the radial apposition, distribution and extremities of strain during crimping to various catheter diameters, and strain differential during compression to a functional implantation diameter and simultaneous axial pushing and pulling by 6% length variation.

These examples are presented to be illustrative of the types of devices which may be formed and various other devices which may be formed from the polymeric substrate are also included within this disclosure.

The applications of the disclosed invention discussed above are not limited to certain processes, treatments, or placement in certain regions of the body, but may include an number of other processes, treatments, and areas of the body. Modification of the above-described methods and devices for carrying out the invention, and variations of aspects of the invention that are obvious to those of skill in the arts are intended to be within the scope of this disclosure. Moreover, various combinations of aspects between examples are also contemplated and are considered to be within the scope of this disclosure as well.

What is claimed is:

1. A method of forming an expandable stent scaffold, comprising:
   dissolving a raw polymeric resin in a solvent to form at least a first polymeric solution, wherein the resin has a molecular weight ranging from about 259,000 g/mol to about 2,120,000 g/mol;
   forming at least a first layer of a biocompatible polymer tube having a first diameter with the first polymeric solution;
   curing the tube;
   processing the tube to form an expandable scaffold having the first diameter and an initial radial strength;
   reducing the first diameter of the expandable scaffold to a second diameter, wherein a radial strength of the expandable scaffold is reduced to a second radial strength less than the initial radial strength upon reduction from the first diameter to the second diameter, wherein the scaffold retains at least 90% of the molecular weight of the resin and at least a portion of a crystallinity of the resin such that the expandable scaffold exhibits ductility upon application of a load; and wherein the expandable scaffold is formed such that a tensile strain at yield of the expandable scaffold is between about 3% and 4%, wherein the expandable scaffold regains 30% to 60% of the initial radial strength of the expandable scaffold after deployment;

wherein the expandable scaffold comprises a plurality of circumferential support elements and a plurality of coupling elements, wherein at least one of the coupling elements extends between a first trough of a first circumferential support element and a second trough of a second circumferential support element, wherein the second trough is connected to the at least one of the coupling elements and is defined by a trough undulation having a distal curved radius along a distal side of the trough undulation, wherein the distal curved radius is between 0.0001 in to 0.75 in;

wherein the first trough forms a radiused extension portion where the at least one of the coupling elements joins a distal side of the first circumferential support element, wherein the radiused extension portion has a radius between 0.0001 in and 0.75 in; and wherein the stent scaffold defines a surface area of 3 $mm^2$ to 3000 $mm^2$ over an outer surface of the stent which contacts a vessel wall, wherein the stent scaffold further defines a total surface area of the stent of 20 $mm^2$ to 12,000 $mm^2$.

2. The method of claim 1, wherein after curing the tube, the method further comprises:
subjecting the tube to a first elevated temperature at or above a glass transition temperature of the tube; and
cooling the tube in a controlled manner to a second temperature lower than the glass transition temperature such that the tube transitions to a glass state and imparts a shape memory effect.

3. The method of claim 2, wherein subjecting the tube to a first elevated temperature comprises subjecting the tube to the first elevated temperature above the glass transition temperature of the tube while reducing the first diameter.

4. The method of claim 1, wherein forming the biocompatible polymer tube comprises immersing a mandrel into the first polymeric solution such that at least the first layer of a biocompatible polymer tube is formed upon the mandrel having the first diameter defined by the mandrel.

5. The method of claim 1, wherein forming the biocompatible polymer tube comprises immersing a mandrel into the first polymeric solution multiple times and further comprising:
controlling a number of immersions of the mandrel into the first polymeric solution;
controlling a duration of time of each immersion of the mandrel;
controlling a delay time between each immersion of the mandrel; and
controlling a withdrawal rate of the mandrel from the first polymeric solution after each immersion.

6. The method of claim 4, wherein immersing the mandrel further comprises immersing the mandrel into a second polymeric solution such that a second layer of polymer is formed upon the first layer.

7. The method of claim 1, wherein reducing the first diameter of the expandable scaffold comprises crimping the expandable scaffold on a balloon catheter.

8. The method of claim 1, wherein reducing the first diameter of the expandable scaffold comprises crimping the expandable scaffold from the first diameter to the second diameter of about 1.2 mm.

9. The method of claim 8, further comprising axially contracting the expandable scaffold by about 6% of the initial length of the expandable scaffold while simultaneously reducing the first diameter of the expandable scaffold to the second diameter of about 1.2 mm.

10. The method of claim 1, wherein reducing the first diameter of the expandable scaffold comprises crimping the expandable scaffold from the first diameter to the second diameter of about 1.1 mm.

11. The method of claim 10, further comprising axially contracting the expandable scaffold by about 6% of the initial length of the expandable scaffold while simultaneously reducing the first diameter of the expandable scaffold to the second diameter of about 1.1 mm.

12. The method of claim 1, wherein the diameter of the expandable scaffold is expanded between about 80% to 250% when the expandable scaffold is expanded from the second diameter to a deployment diameter.

13. The method of claim 1, wherein processing the biocompatible polymer tube to form the expandable scaffold comprises laser cutting a scaffold design comprising a plurality of undulating circumferential support elements connected by linking elements.

14. The method of claim 1, wherein the expandable scaffold regains 30% to 60% of the initial radial strength of the expandable scaffold within about seven months after deployment.

15. The method of claim 1, further comprising coating the expandable scaffold with sirolimus.

16. The method of claim 1, wherein the diameter of the expandable scaffold is expanded by about 80% when the expandable scaffold is expanded from the second diameter to a deployment diameter.

17. A method of forming an expandable stent scaffold, comprising:
dissolving a raw polymeric resin in a solvent to form at least a first polymeric solution, wherein the resin has a molecular weight ranging from about 259,000 g/mol to about 2,120,000 g/mol;
forming at least a first layer of a biocompatible polymer tube having a first diameter with the first polymeric solution;
curing the tube;
processing the tube to form an expandable scaffold having the first diameter and an initial radial strength;
reducing the first diameter of the expandable scaffold to a second diameter, wherein a radial strength of the expandable scaffold is reduced to a second radial strength less than the initial radial strength upon reduction from the first diameter to the second diameter; and
wherein the expandable scaffold is formed such that a tensile strain at yield of the expandable scaffold is between about 3% and 4%,
wherein the expandable scaffold regains 30% to 60% of the initial radial strength of the expandable scaffold after deployment; and
wherein the expandable scaffold comprises a plurality of circumferential support elements and a plurality of coupling elements, wherein at least one of the coupling elements extends between a first trough of a first circumferential support element and a second trough of a second circumferential support element, wherein the second trough is connected to the at least one of the coupling elements and is defined by a trough undulation having a distal curved radius along a distal side of the trough undulation, wherein the distal curved radius is between 0.0001 in to 0.75 in, wherein the second trough forms a first proximal radius where the at least one of the coupling elements joins the second circumferential support element, wherein the first proximal radius is between 0.0001 in to 0.75 in, wherein the second trough forms a second proximal radius where the at least one of the coupling elements joins the second circumferential support element, wherein the second proximal radius is between 0.0001 in to 0.75 in, wherein the first proximal radius is on a first side of the second circumferential support element and the second proximal radius is on a second side of the second circumferential support element, wherein the first and second sides of the second circumferential support element are on opposite sides of the second circumferential support element, wherein a distance between the first proximal radius and the second proximal radius is between 0.0005 in to 0.75 in.

18. The method of claim 17, further comprising axially extending the expandable scaffold by about 6% of the initial length of the expandable scaffold while simultaneously reducing the first diameter of the expandable scaffold to the second diameter of about 1.2 mm.

19. The method of claim 17, further comprising axially extending the expandable scaffold by about 6% of the initial length of the expandable scaffold while simultaneously reducing the first diameter of the expandable scaffold to the second diameter of about 1.1 mm.

* * * * *